US010898662B2

(12) United States Patent
Huddart et al.

(10) Patent No.: US 10,898,662 B2
(45) Date of Patent: Jan. 26, 2021

(54) PATIENT INTERFACE WITH VENTING

(71) Applicant: FISHER & PAYKEL HEALTHCARE LIMITED, Auckland (NZ)

(72) Inventors: Brett John Huddart, Auckland (NZ); Ronald Gane, Auckland (NZ); Callum Ross Gordon, Auckland (NZ); Mark Andrew Thompson, Auckland (NZ); Thomas Mark Richardson, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 1076 days.

(21) Appl. No.: 14/769,674

(22) PCT Filed: Feb. 21, 2014

(86) PCT No.: PCT/NZ2014/000021
§ 371 (c)(1),
(2) Date: Aug. 21, 2015

(87) PCT Pub. No.: WO2014/129913
PCT Pub. Date: Aug. 28, 2014

(65) Prior Publication Data
US 2016/0008558 A1 Jan. 14, 2016

Related U.S. Application Data

(60) Provisional application No. 61/767,586, filed on Feb. 21, 2013, provisional application No. 61/845,102, filed on Jul. 11, 2013.

(51) Int. Cl.
A61M 16/00 (2006.01)
A61M 16/08 (2006.01)
(Continued)

(52) U.S. Cl.
CPC ........ *A61M 16/0003* (2014.02); *A61M 16/06* (2013.01); *A61M 16/0683* (2013.01);
(Continued)

(58) Field of Classification Search
CPC .............. A61M 16/06; A61M 2205/42; A61M 16/0683
(Continued)

(56) References Cited

U.S. PATENT DOCUMENTS 4,574,799 A * 3/1986 Warncke ................ A62B 18/02
128/206.24
5,460,174 A * 10/1995 Chang .................... A62B 9/022
128/204.25
(Continued)

FOREIGN PATENT DOCUMENTS

DE 297 23 101 1/1998
EP 0697225 2/1996
(Continued)

OTHER PUBLICATIONS

European Patent Office, Extended European Search Report, Application No. 18163847.9-1122, dated Jul. 23, 2018, in 7 pages.
(Continued)

Primary Examiner — Timothy A Stanis
Assistant Examiner — Victoria Murphy
(74) Attorney, Agent, or Firm — Knobbe, Martens, Olson and Bear, LLP

(57) ABSTRACT

Interfaces for positive pressure therapy having various vent designs are disclosed herein. The interfaces include a bias flow vent with design geometries that help reduce and/or minimize draft and noise levels of the fluids exiting the vents. Some of the vent designs include particular vent hole geometries, plenum spaces, diffusers and fibrous media.

41 Claims, 32 Drawing Sheets

(51) Int. Cl.
*A61M 16/06* (2006.01)
*A61M 16/20* (2006.01)

(52) U.S. Cl.
CPC ..... *A61M 16/0825* (2014.02); *A61M 16/0616* (2014.02); *A61M 16/0633* (2014.02); *A61M 16/0866* (2014.02); *A61M 16/208* (2013.01); *A61M 2205/42* (2013.01)

(58) Field of Classification Search
USPC .................................................. 128/207.12
See application file for complete search history.

(56) References Cited

U.S. PATENT DOCUMENTS

| | | | | |
|---|---|---|---|---|
| 5,924,420 | A * | 7/1999 | Reischel | A62B 18/08 |
| | | | | 128/206.21 |
| 6,192,886 | B1 * | 2/2001 | Rudolph | A61M 16/06 |
| | | | | 128/205.25 |
| 6,581,594 | B1 | 6/2003 | Drew et al. | |
| 6,662,803 | B2 | 12/2003 | Gradon et al. | |
| 8,109,271 | B2 * | 2/2012 | Vandine | A61M 16/06 |
| | | | | 128/207.11 |
| 2003/0094177 | A1 | 5/2003 | Smith et al. | |
| 2003/0196658 | A1 * | 10/2003 | Ging | A61M 16/06 |
| | | | | 128/201.22 |
| 2004/0094157 | A1 * | 5/2004 | Dantanarayana | A61B 5/0876 |
| | | | | 128/206.21 |
| 2007/0062536 | A1 * | 3/2007 | McAuley | A61M 16/06 |
| | | | | 128/206.21 |
| 2007/0101998 | A1 | 5/2007 | Kwok et al. | |
| 2008/0210241 | A1 | 9/2008 | Schulz et al. | |
| 2009/0050156 | A1 | 2/2009 | Ng et al. | |
| 2010/0051034 | A1 * | 3/2010 | Howard | A61M 16/06 |
| | | | | 128/206.27 |
| 2011/0146685 | A1 | 6/2011 | Allan et al. | |
| 2012/0285457 | A1 | 11/2012 | Mansour et al. | |
| 2016/0213876 | A1 | 7/2016 | McAuley et al. | |
| 2017/0296770 | A1 | 10/2017 | Gunaratnam et al. | |

FOREIGN PATENT DOCUMENTS

| | | |
|---|---|---|
| EP | 2457518 | 10/2017 |
| WO | WO 2005/021075 | 3/2005 |
| WO | WO 2006/069415 | 7/2006 |
| WO | WO 2011/014931 | 2/2011 |
| WO | WO 2012/052902 | 4/2012 |
| WO | WO 2014/129913 | 8/2014 |

OTHER PUBLICATIONS

International Search Report; PCT/NZ2014/000021; filed Feb. 21, 2014.
Australian Government, Examination Report No. 1, Application No. 2018236891, dated Jun. 25, 2019, in 3 pages.
European Patent Office Examination Report for Application No. 18 163 847.9 dated Jun. 16, 2020, 5 pages.
Written Opinion for PCT/NZ2014/000021 dated May 20, 2014 in 9 pgs.
Australian Examination Report for Patent Application No. 2018236891 dated Jun. 9, 2020.

* cited by examiner

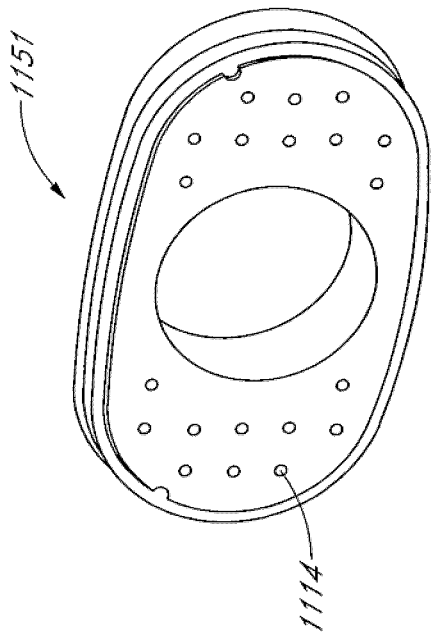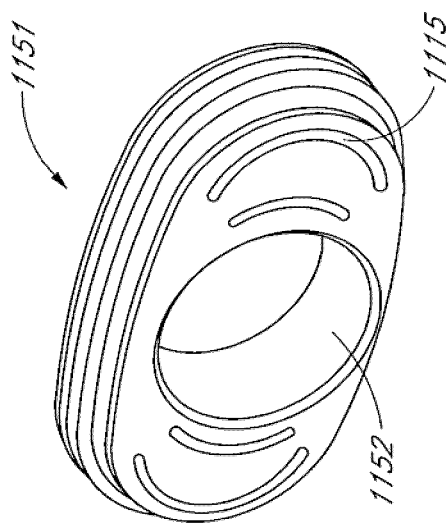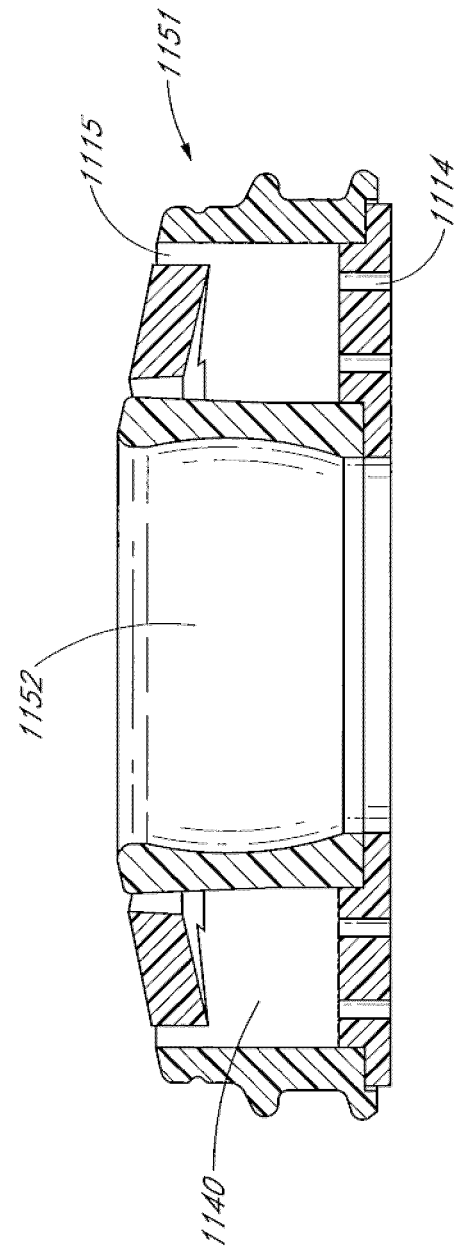
FIG. 22B
FIG. 22A
FIG. 22C

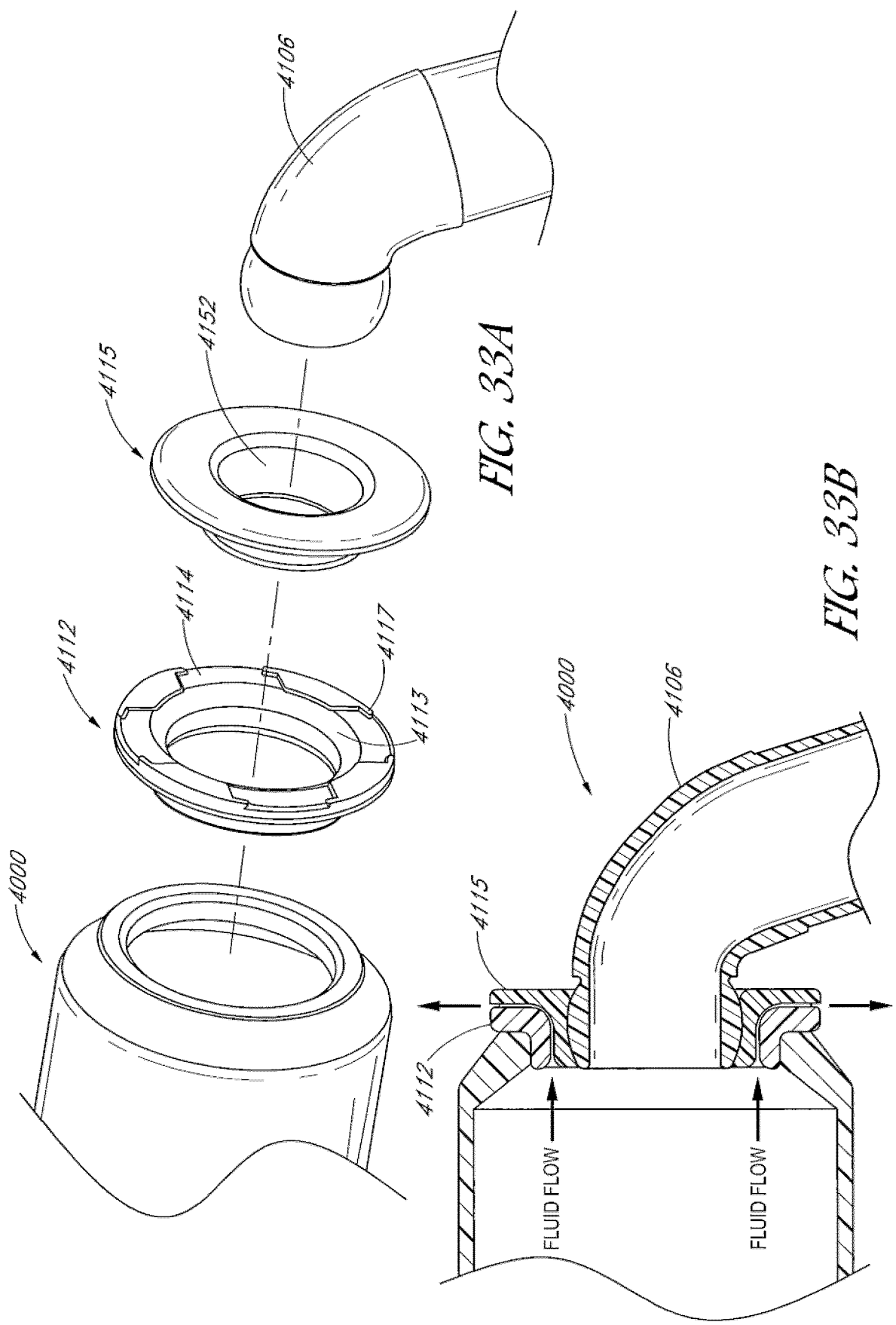

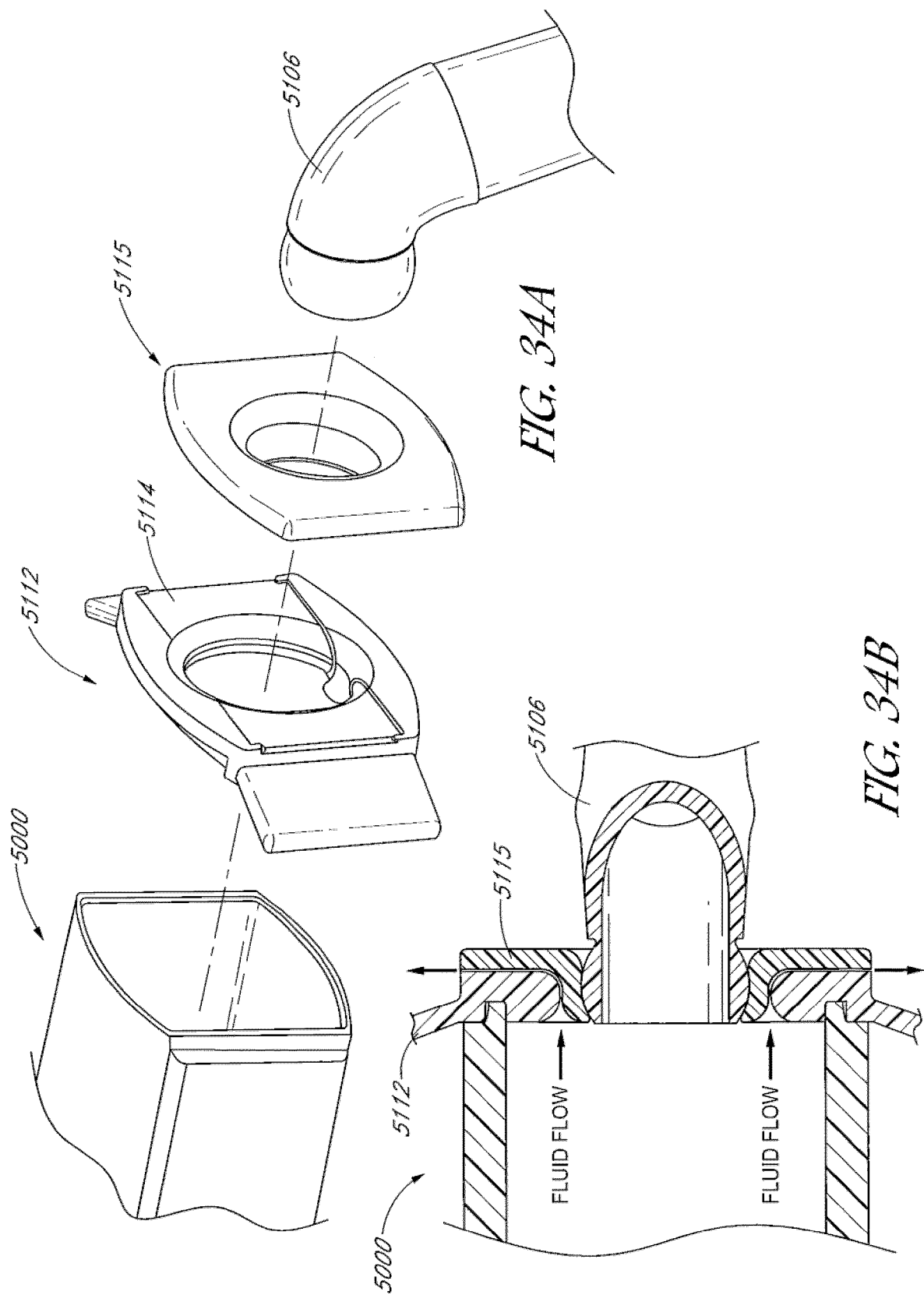

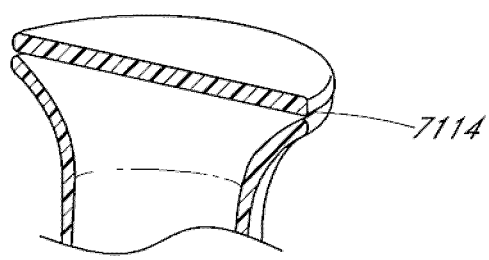
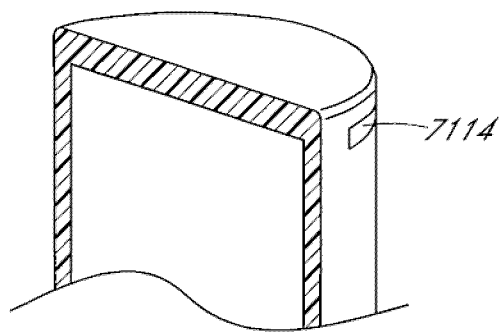
*FIG. 36A*    *FIG. 36B*
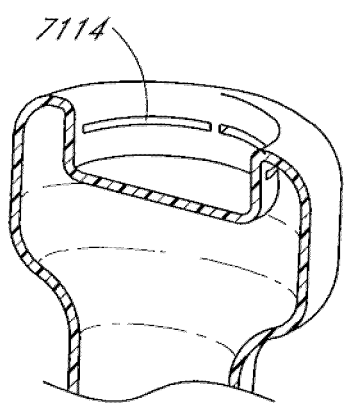
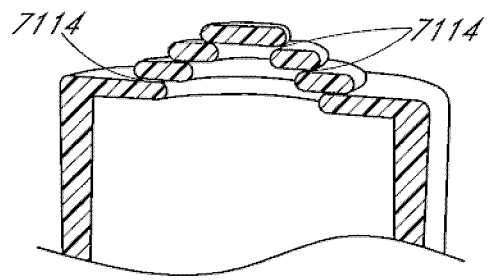
*FIG. 36C*    *FIG. 36D*

PATIENT INTERFACE WITH VENTING

INCORPORATION BY REFERENCE TO ANY PRIORITY APPLICATIONS

Any and all applications for which a foreign or domestic priority claim is identified in the Application Data Sheet as filed with the present application are hereby incorporated by reference and made a part of the present disclosure.

BACKGROUND OF THE INVENTION

Field of the Invention

The present invention generally relates to patient interfaces for respiratory therapy. More particularly, certain aspects of the present disclosure relate to various systems and methods for venting gases from patient interfaces.

Description of the Related Art

The treatment of obstructive sleep apnea (OSA) by continuous positive airway pressure (CPAP) flow generator systems involves the continuous delivery of pressurized gases to the airways of a human via a conduit and an interface (e.g., a mask). Typically the interface creates at least a substantial seal on or around the nose and/or the mouth. As the patient breathes, carbon dioxide gases can progressively accumulate in the delivery system, which if left over a period of time, can become hazardous to the patient.

One solution to this issue is to provide washout vents, also known as bias flow vents, which enable a flow of gases to be exhausted to the atmosphere and provides a mechanism for reducing or removing the accumulation of carbon dioxide gases.

The vents, while providing a mechanism for removing carbon dioxide, also have trade-offs. The vents can create a disturbance for the patient and/or the patient's bed partner. This disturbance typically manifests itself in two forms: noise and the creation of a draft.

SUMMARY OF THE DISCLOSURE

The creation of practical and not-so-practical solutions to the drawbacks of washout vents has been the subject of considerable development effort from numerous organisations which has resulted in numerous patents. However, a need still exists for improved designs.

It is an object of the present disclosure to provide one or more constructions and/or methods that will at least go some way towards improving on the above or that will at least provide the public or the medical profession with a useful choice. The following is a description of a number of practical options to improve current designs.

In accordance with at least one of the embodiments disclosed herein, a patient interface is provided comprising a body portion sized and shaped to surround the nose and/or mouth of a user and adapted to create at least a substantial seal with the user's face, a coupling that permits the patient interface to be coupled to a gas delivery system, and a vent that allows the passage of gas from an interior of the body portion to an exterior of the body portion, the vent comprising a plurality of exit holes arranged in an array.

A diameter of each of the plurality of exit holes can be between about 0.5 mm and about 1.5 mm. A length to diameter ratio of each of the plurality of exit holes can be at least about 2. A ratio of a pitch distance between each of the plurality of exit holes to the diameter can be at least about 4. An exit radius of each of the plurality of exit holes can be at least about 0.5 mm. An entry radius of each of the plurality of exit holes can be at least about 0.5 mm.

In some configurations, the gas that exits the vent enters directly into a plenum chamber defined by the patient interface. The plenum chamber can be defined between the body portion and a frame portion or a shroud of the patient interface. The plenum space can also contain a fibrous media.

In some configurations, the vent is located on the coupling and the plenum chamber is defined between the coupling and a shroud that at least partially surrounds the coupling. The coupling can be a ball-jointed elbow or a swiveling joint.

In some configurations, the gas that exits the vent enters a diffuser. The diffuser can be frustoconical in shape. The diffuser can have an expansion angle of at least about 4 degrees and/or less than or equal to about 8 degrees. The length to root diameter ratio of the diffuser can be at least about 1.5 to 1.

In accordance with at least one of the embodiments disclosed herein, a patient interface is provided comprising a body portion sized and shaped to surround the nose and/or mouth of a user and adapted to create at least a substantial seal with the user's face, a coupling that permits the patient interface to be coupled to a gas delivery system, a vent that allows the passage of gas from an interior of the body portion to an exterior of the body portion, the vent comprising a plurality of exit holes arranged in an array, and a plenum chamber that receives the gas exiting the vent.

In some configurations, the plenum chamber is configured to return the exit gas flow back on itself. The plenum chamber can have a cone angle of between about 4 degrees and about 8 degrees. The plenum chamber can have a length to root diameter ratio of at least about 1.5 to 1.

In some configurations, the plenum chamber is defined between the body portion and a frame portion or a shroud of the patient interface. The frame portion or the shroud can be positioned between about 3 to about 5 hole diameters from the vent. The frame portion or the shroud can define a textured surface facing the vent.

In some configurations, the vent is located on the coupling and the plenum chamber is defined between the coupling and a shroud that at least partially surrounds the coupling. The coupling can be a ball-jointed elbow. The shroud can be positioned between about 3 to about 5 hole diameters from the vent. The shroud can define a textured surface facing the vent.

In some configurations, the plenum chamber re-directs the gas flow through an angle of between 45 degrees and about 135 degrees. The plenum chamber at the exit point of the gas flow to ambient can form a sharp corner between the inner surface and the adjoining surface. The plenum chamber at the exit point of the gas flow to ambient can have a radius applied to the corner between the inner surface and the adjoining surface.

In some configurations, the plenum chamber is defined as the space between the body portion or cap and a frame portion of the patient interface. The plenum chamber can be in the shape of an annulus.

In some configurations, the plenum space also contains a fibrous media. All of the vented gas exiting the plenum space into the ambient space can pass through the fibrous media.

In accordance with at least one of the embodiments disclosed herein, a patient interface is provided comprising a body portion sized and shaped to surround the nose and/or mouth of a user and adapted to create at least a substantial seal with the user's face, a coupling that permits the patient interface to be coupled to a gas delivery system, a vent that allows the passage of gas from an interior of the body portion to an exterior of the body portion, the vent comprising a plurality of exit holes arranged in an array, and a textured/fibrous surface defined by a component of the patient interface located in front of and facing the vent.

In some configurations, the component is a shroud or a frame portion or an extra component. The textured surface can be located between about 3 hole diameters and about 5 hole diameters from the vent.

In accordance with at least one of the embodiments disclosed herein, a patient interface is provided comprising a body portion sized and shaped to surround the nose and/or mouth of a user and adapted to create at least a substantial seal with the user's face, a coupling that permits the patient interface to be coupled to a gas delivery system, wherein the coupling comprises a rotational joint, and a vent that allows the passage of gas from an interior of the body portion to an exterior of the body portion, wherein the vent comprises a plurality of passages incorporated in the rotational joint of the coupling.

In some configurations, the rotational joint can be a swivel joint. In other configurations, the rotational joint can be a ball joint.

In some configurations, the plurality of passages can be formed in the female portion of the coupling. The plurality of passages that are formed in the female portion of the coupling can be combined with a gutter or leak channel.

In other configurations, the plurality of passages can be formed on the male portion of the coupling. The plurality of passages that are formed on the male portion of the coupling can extend sufficiently to prevent occlusion when the coupling is positioned at the extremes of motion.

BRIEF DESCRIPTION OF THE DRAWINGS

Specific embodiments and modifications thereof will become apparent to those skilled in the art from the detailed description herein having reference to the figures that follow, of which:

FIG. 22A is a front perspective view of a ball socket component with a plenum space, according to an embodiment of the present disclosure.

FIG. 22B is a back perspective view of the ball socket component of FIG. 22A.

FIG. 22C is a cross-sectional view of the ball socket component of FIG. 22A.

FIG. 33A is an exploded view of an interface with slots, according to an embodiment of the present disclosure.

FIG. 33B is a cross-sectional view of the interface of FIG. 33A.

FIG. 34A is an exploded view of an interface with slots, according to another embodiment of the present disclosure.

FIG. 34B is a cross-sectional view of the interface of FIG. 34A.

FIGS. 36A-F are cross-sectional view of various embodiments of slots.

DETAILED DESCRIPTION OF SPECIFIC EMBODIMENTS

Figure 1:
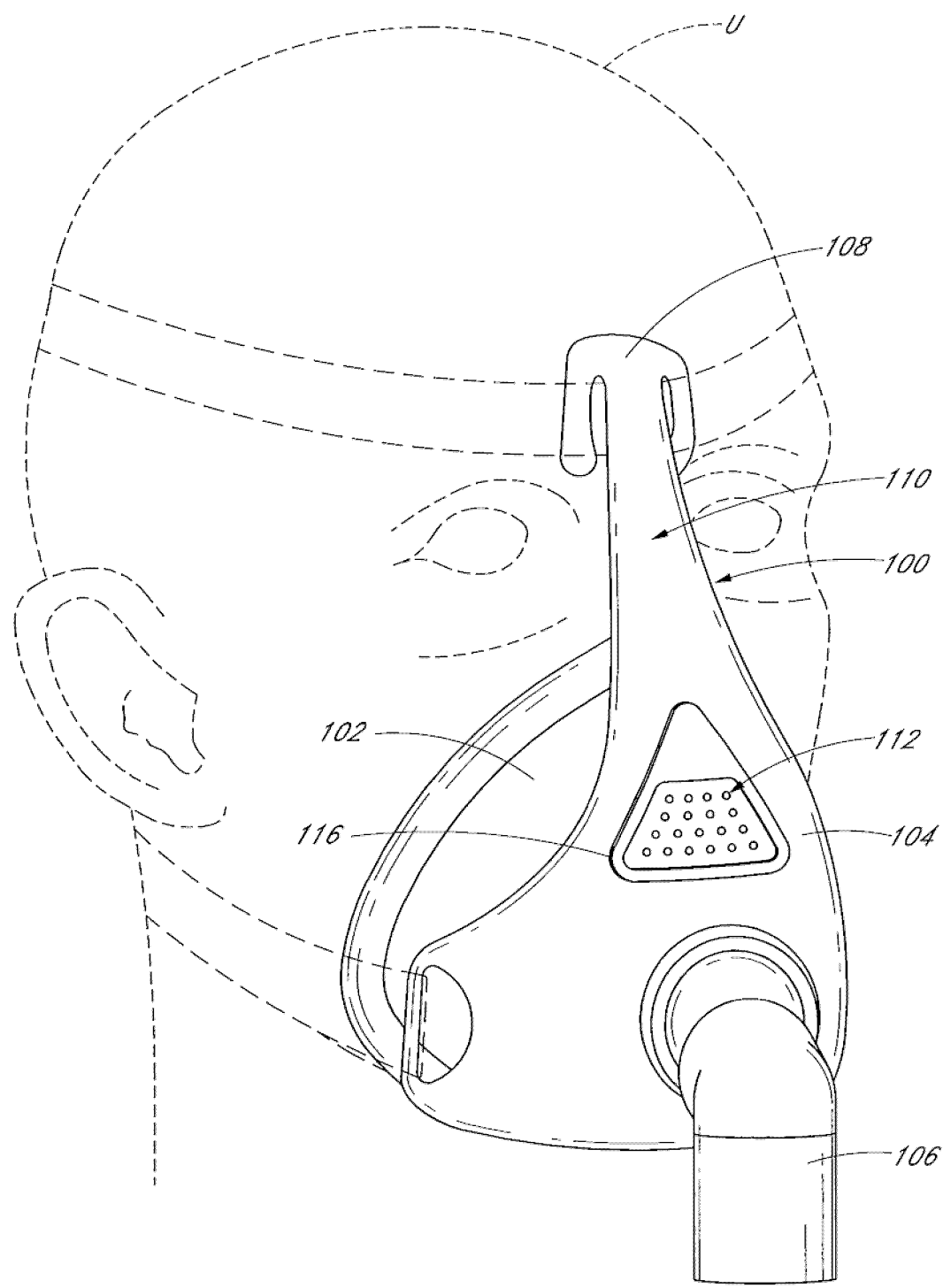
FIG. 1 is a perspective view of a respiratory interface on a patient's head.

With reference initially to FIG. 1, an embodiment of an interface 100 is illustrated on a user U. The interface 100 can be used in the field of respiratory therapy. In some embodiments, the interface 100 has particular utility with forms of positive pressure respiratory therapy. For example, the interface 100 can be used for administering continuous positive airway pressure ("CPAP") treatments, variable positive airway pressure ("VPAP") treatments and/or bi-level positive airway pressure ("BiPAP") treatments. The interface can be compatible with one or more different types of suitable CPAP systems.

The interface 100 can comprise any of a plurality of different types of suitable mask configurations. For example, certain features, aspects and advantages of the present invention can be utilized with nasal masks, full face masks, oronasal masks or any other positive pressure mask. Although the illustrated mask is a full face mask, the scope of the present disclosure should not be limited by the particular embodiments described.

In the illustrated configuration, the interface 100 comprises a mask body 102, a mask frame 104 and a connection port assembly 106. The mask body 102 is configured to cover the user's mouth and/or nose to deliver respiratory gases to the user. The mask body 102 can be secured to the mask frame 104. The mask frame 104 is held in place by a headgear assembly that wraps around the user's head. A connection port assembly 106 can be connected to the mask body 102 and/or mask frame 104, preferably with a releasable connection. In some configurations, the connection port assembly 106 can include a ball joint to improve flexibility and comfort.

The mask frame 104 can couple to the mask body 102 and help stabilize the interface 100 on the user's face. The mask frame 104 can be any shape and size to functionally secure the interface 100 to the user's face. The mask frame 104 can be attached to the mask body 102 with interlocking clips, tabs or other functional couplers. The mask frame 104 can be rigid, substantially rigid or semi-rigid to provide support for the mask body 102. For example, the mask frame 104 can be at least partially made of a metal or rigid plastic, such as acrylic, polycarbonate or high-density polyethylene.

As illustrated in FIG. 1 the mask frame 104 can extend to the user's forehead and include a forehead rest 108. The forehead rest 108 can help stabilize the interface 100 to the user's face by providing a support point for the interface 100 and connection points for the headgear assembly. In the illustrated configuration, a frame bridge 110 extends from the main body of the frame and is connected to the forehead rest 108. The frame bridge 110 can be integrally formed or molded with the rest of the mask frame 104 from the same rigid material.

In some configurations, the forehead rest 108 can be a separate flexible piece that is attached or overmoulded onto the mask frame 104. For example, the forehead rest 108 can be made of a flexible silicone that is overmoulded onto the frame bridge 110. The flexible material advantageously conforms to the user's forehead anatomy and helps improve comfort to the user with soft material contact. In some configurations, the forehead rest 108 can be attached or integrally formed as part of the mask frame 104 and can be made of the same material as the mask frame 104 and frame bridge 110.

The typical method of passively venting carbon dioxide ($CO_2$) is via the use of a hole or a hole array that is incorporated into the mask body or gas path componentry that, for example, is directly connected to the mask. In the embodiment illustrated in FIG. 1, the interface 100 has vents 112 for expelling gases from inside the mask to the environment. The vents 112 can help expel carbon dioxide gases from the user to reduce the rebreathing of the carbon dioxide gases.

The vents 112 create a controlled or known leak to enable the exhausting of the user's exhaled carbon dioxide gases. There may be a performance trade-off between the location of the vents (relative to the patient's mouth or nose) and the amount of bias flow required. As used herein, bias flow refers to the flow of gases to the environment through the vents. The flow rate of the bias flow and the design geometry of the vent holes can have an effect on the noise level and draft that the bias flow produces, as well as the amount of entrainment that the exiting gas flow may cause, as discussed further below.

In the illustrated configuration, the vents 112 comprise a plurality of through holes on the mask body 102 that expel gases through a cutout 116 in the mask frame 104. In other configurations, the vents can be slits or large openings instead of or in addition to small through holes. In some configurations, the vents can be disposed on other portions of the interface, such as the connection port assembly or connection joints, as discussed below. Generally, relatively smaller hole sizes produce less airflow noises compared to a larger hole size given the same flow velocity through both hole sizes. The plurality of holes helps reduce airflow noises compared to having one or a few holes with the same vent area when expelling a given volume of gas.

In some embodiments, the vents 112 can be formed as a separate component from the mask body or mask frame. The separate vent module can be permanently or releasably assembled to the mask body or mask frame. For example, the vent module can have threads that mate with complementary threads on the mask body. In other configurations, the air vent module can have any type of functional coupler to mate the vent module to the mask body or mask frame. In these configurations, the vent module can be removed easily for service, cleaning or replacement.

The vent module can be overmoulded to the mask body or mask frame for a permanent attachment. The overmoulding can include a flexible gusset between the vent module and the mask that helps with flexibility. In other configurations, the vent module can be permanently attached using, for example, adhesives or ultrasonic welding.

Furthermore, the vents 112 can be formed of a different material than the mask body or mask frame. This can advantageously allow the vents to be made of a material that is suitable for forming apertures. For example, the vents can be made of a soft and/or flexible material while the mask body and/or mask frame are made of a more rigid material. In some configurations, the soft and/or flexible material (e.g., silicone, rubber, foam and the like) may help reduce the amount of noise the flow makes through the apertures. However, in some embodiments, the vents 112 can be formed of the same material as the mask body and/or mask frame while providing acceptable noise and draft levels.

A separate vent module advantageously allows improved manufacturing and product quality. By having the vents in a separate component the moulding of the small and detailed vent apertures can be better controlled. By moulding the vents as a separate component, the part tolerances can be better controlled and result in more consistent hole dimensions having a more consistent flow rate performance between parts. Moulding a separate vent module may allow for production of more complex vent designs as a result of not having to accommodate undercuts and other geometric restrictions of other components, such as the mask body for example. Improved control of the part dimensions may also improve control of noise levels, such as by controlling the part contours to produce a smooth air flow through the holes.

It has been learned that optimizing the design of the vent hole geometry and the adjoining plenum chamber can be beneficial in reducing the noise and draft levels of the fluids exiting the vents. Various definitions can be used to quantify or measure sound levels.

First, sound power can be used to quantify the sound levels. This is the measure of the amount of energy from a particular sound source. The measurement is independent of distance from the sound source. Second, sound pressure can be used to quantify sound levels. This is the measure of the intensity of the sound at a particular distance from the sound source. This is typically measured in decibels (i.e., dB or dBa). A third method of quantifying sound levels is a sound field. A sound field is a graphical representation (i.e., a contour map) of the pressure levels of a particular sound as a function of position from the sound source.

Figure 2:
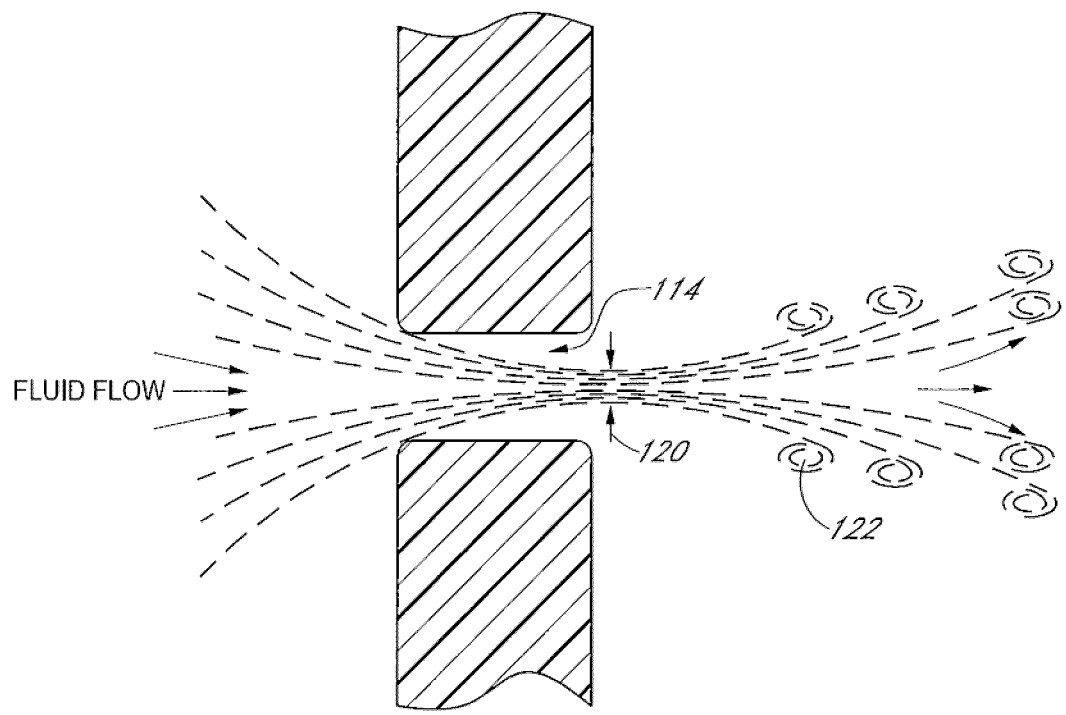
FIG. 2 shows an example of a fluid flow through a vent hole.

FIG. 2 illustrates an example of a fluid flow passing through a vent hole 114. As used herein, the term fluid is used to refer to liquids, gases or a combination of liquids and gases. During the process of flowing through the vent hole 114 a complex set of fluid dynamics occurs, for which there is considerable digital and experimental based data sets to describe its behaviour.

When a fluid flow experiences a sudden contraction in the flow path, such as with vent holes, the flow contracts through a minimum cross-section called the vena contracta 120, as illustrated in FIG. 2. The position of the vena contracta 120 is downstream of the vent hole 114 entrance. Substantially all the fluids that passes through the vent hole 114 will pass through the vena contracta 120 and this location is also the location of highest flow velocity and lowest pressure.

As the fluid flow exits the vena contracta 120, it progressively reduces in velocity and increases in pressure, until it reaches a velocity of approximately zero and a pressure of approximately atmospheric pressure. In this transition zone after the vena contracta 120, vortices 122 may form at the boundary between the exiting fluid flow and the stationary atmospheric air, which are caused by viscous effects between the two fluids being at different velocities. This effect is known as vortex shedding. At a macro level, the vortex shedding may produce rapid random fluctuations which occur across a range of frequencies. Typically, the frequencies can range from at least approximately 1 kHz to less than or equal to 10 kHz, with wavelengths in the range of at least approximately 1 mm to less than or equal to 4000 mm.

Figure 3:
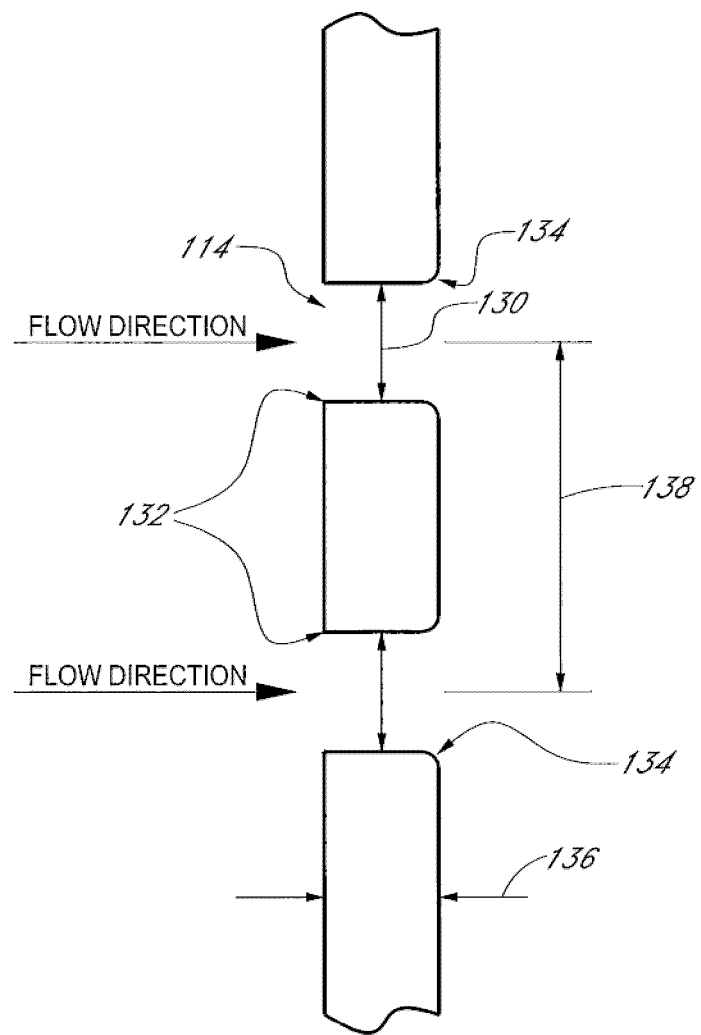
FIG. 3 is a cross-sectional view of vent holes according to an embodiment of the present disclosure.

There are a number of geometric factors that influence the amount of sound energy created by the vortex shedding. These geometric variables can be utilised during the design of the vent holes 114 to reduce and minimise the amount of sound energy created when fluids travel through the vents 112. With reference to FIG. 3, the variables can include: (1) The flow rate through the vent hole 114, which is a function of the hole diameter 130 and the pressure drop from the entrance to the exit of the vent hole; (2) The quality of the vent hole, which can be characterised by the smoothness of the hole and the absence of debris in the hole; (3) The geometry of the hole, particularly the entrance radius 132 and exit radius 134 of the hole, and the hole length 136 to diameter 130 ratio of the hole; (4) The geometry of the hole array, for example the hole pitch 138 (i.e., the distance between vent holes).

The two most commonly understood flow types are laminar flow and turbulent flow, which can be quantified by a Reynolds number. For design purposes, the Reynolds number at which the transition between laminar flow and turbulent flow occurs is approximately 2300. In situations where turbulent flow occurs at the vena contracta, there is usually an increase in sound level. Furthermore, when debris or surface imperfections exist in the vent holes, this can create a mechanism that promotes an earlier transition from laminar flow to turbulent flow compared to smooth surface vent holes.

Figure 4:
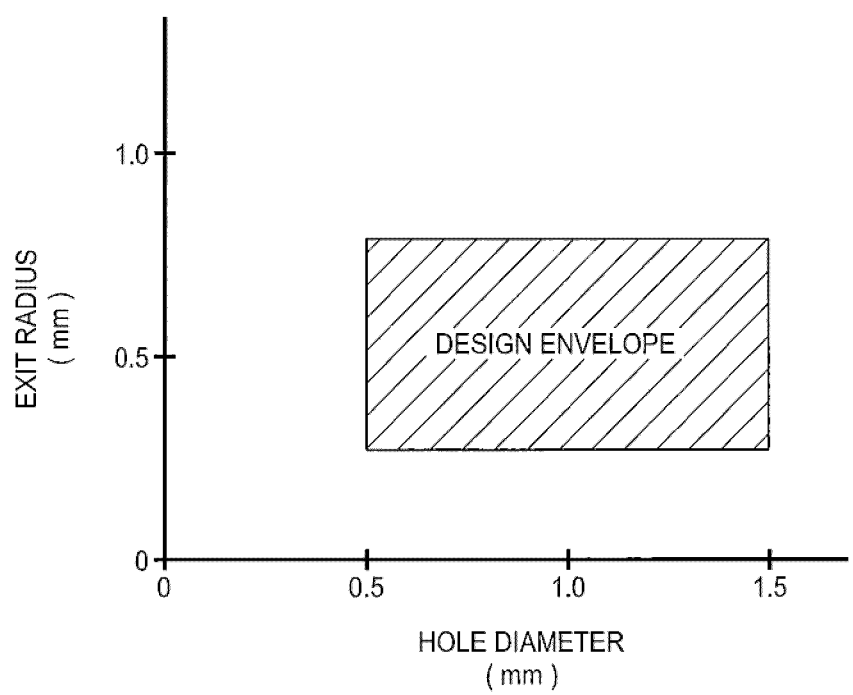
FIG. 4 shows a graphical representation of a design envelope for exit radius versus hole diameter for vent holes.

Being able to adjust the geometry of the vents offers the ability to control the sound levels produced by the vents to be within an acceptable range for use as part of a CPAP system. Some design envelopes have been developed that achieve acceptable sound levels. One of the design envelopes is for the vent hole diameter 130 versus the exit radius 134. A graphical representation of the design envelope showing vent hole diameter versus the exit radius is illustrated in FIG. 4.

The contour of the exit radius 134 can affect the noise levels that are created by the fluid flow. In some configurations, the exit radius 134 can be at least approximately 0.25 mm and/or less than or equal to approximately 0.75 mm. As discussed below, this range is preferable for reducing or minimizing the noise levels created by a 1 mm vent hole. Similarly, the contour of the entrance radius can affect the noise levels that are created by the fluid flow. In some configurations, the entrance radius can be at least approximately 0.25 mm. In some configurations, the entrance radius can be at least approximately 0.1 mm and/or less than or equal to approximately 1 mm.

Figure 5:
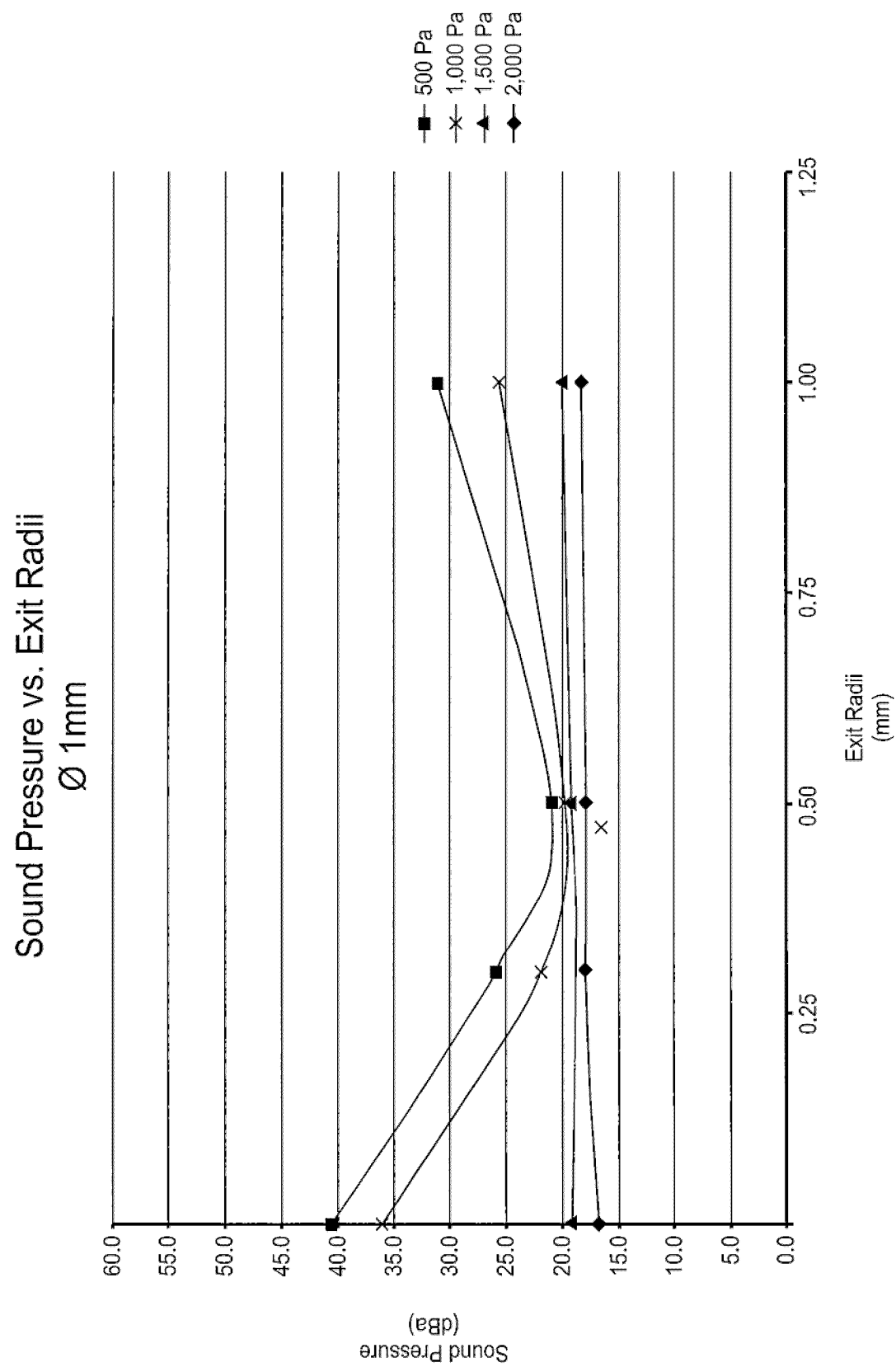
FIG. 5 is a graph showing sound pressure versus exit radii for a 1 mm vent hole.

FIG. 5 illustrates a graph illustrating sound pressure versus exit radius for a 1 mm vent hole. As shown in the graph, sound levels are relatively high when the exit radius is zero. The sound levels steadily decrease to a minimum sound level at approximately 0.5 mm exit radius. The sound levels slowly increase as the exit radius is increased. A range of approximately 0.25 mm and/or less than or equal to approximately 0.75 mm has been found to be a range that provides acceptable noise levels.

The contour of the exit radius 134 can also substantially reduce the variation in the noise level that is created as the flow rate is changed. The noise level can have minimal variation as the driving pressure from the CPAP unit changes. Accordingly, the vent can have a substantially constant sound output that is predictable throughout a range of driving pressures. The entrance radius 132 has similar effects on the sound power level, although a less pronounced effect compared to the exit radius 134.

In some configurations, the hole diameter 130 can be at least approximately 0.5 mm and/or less than or equal to approximately 1.5 mm. Producing vent hole diameters smaller than 0.5 mm can be difficult or impractical using conventional injection molding techniques. With vent hole diameters larger than 1.5 mm, the sound power created by the gas flow can produce sound pressure levels larger than what is acceptable for some applications.

Although FIG. 4 illustrates a preferable design envelope to achieve desirable sound levels produced by the vents, in some configurations the ranges for vent hole diameter and exit radius can be broader while still achieving acceptable sound levels. For example, in some configurations, the exit radius can be at least approximately 0.1 mm and/or less than or equal to approximately 1 mm. Furthermore, in some configurations, the hole diameter can be at least approximately 0.25 mm and/or less than or equal to approximately 2 mm.

Figure 6:
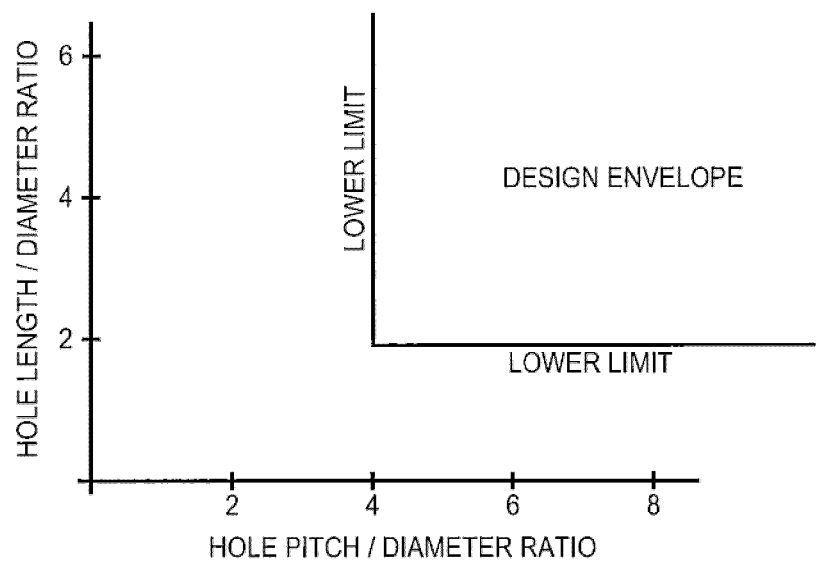
FIG. 6 shows a graphical representation of a design envelope for hole length/diameter ratio versus hole pitch/diameter ratio for vent holes.

Another design envelope is for hole pitch/diameter ratio versus the hole length/diameter ratio. A graphical representation of the design envelope showing hole pitch/diameter ratio versus the hole length/diameter ratio is illustrated in FIG. 6.

In some configurations, the vent hole length to diameter ratio can be at least approximately 2. Having a hole length to diameter ratio below 2 may significant increase the sound power level for a given hole size. For example, a hole length to diameter ratio of 1.5 can approximately doubles the decibel sound output compared to a ratio of 2. However, in some configurations, the vent hole length to diameter ratio can be at least approximately 1 while still providing acceptable sound levels.

Figure 7:
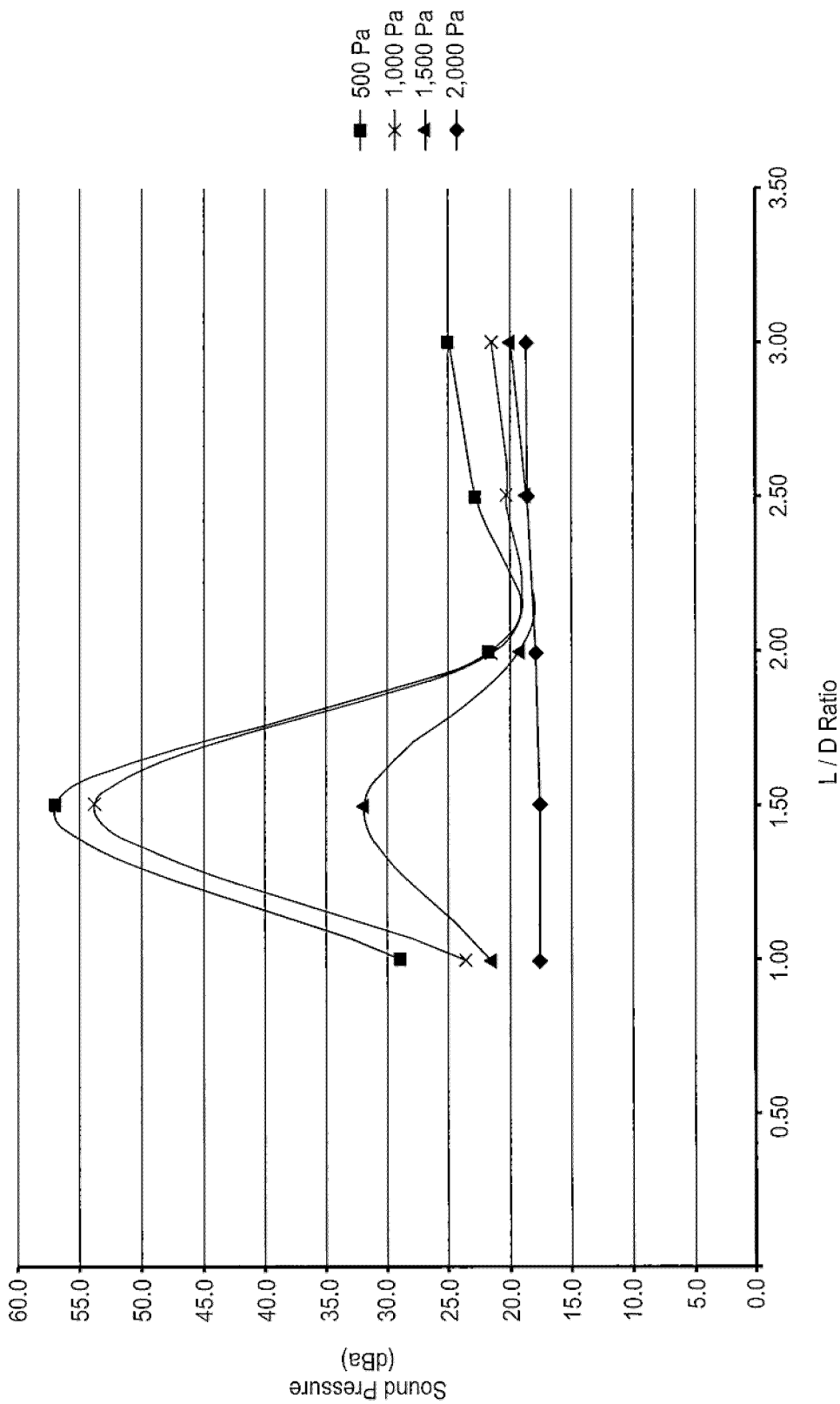
FIG. 7 is a graph showing sound pressure versus length/diameter ratio for a 1 mm vent hole having a 0.5 mm exit radius.

FIG. 7 is a graph showing sound pressure versus length/diameter ratio for a 1 mm vent hole having a 0.5 mm exit radius. As shown in the graph, sound levels are relatively low at a length/diameter ratio of approximately 1. The sound levels rapidly increase to a maximum sound level at a ratio of approximately 1.5. The sound levels rapidly decrease to a minimum at a ratio of approximately 2. The sound levels slowly increase as the ratio increases above 2. Accordingly, a range for the length/diameter ratio of greater than approximately 2 has been found to be an acceptable range for minimizing noise levels.

Once the design has been established for a single hole and the resulting flow rate for that hole is established, the number of holes required for sufficient carbon dioxide flushing can be determined. Multiple vent holes can be positioned in a vent hole array. In some configurations, the vent hole pitch (i.e., the distance between holes) to diameter ratio can be at least approximately 4. Generally, for ratios outside this design envelope, the fluid flows from the individual holes can have a strong interaction with each other, which multiplies the sound output. However, in some configurations, the vent hole pitch to diameter ratio can be at least approximately 3.

Figure 8:
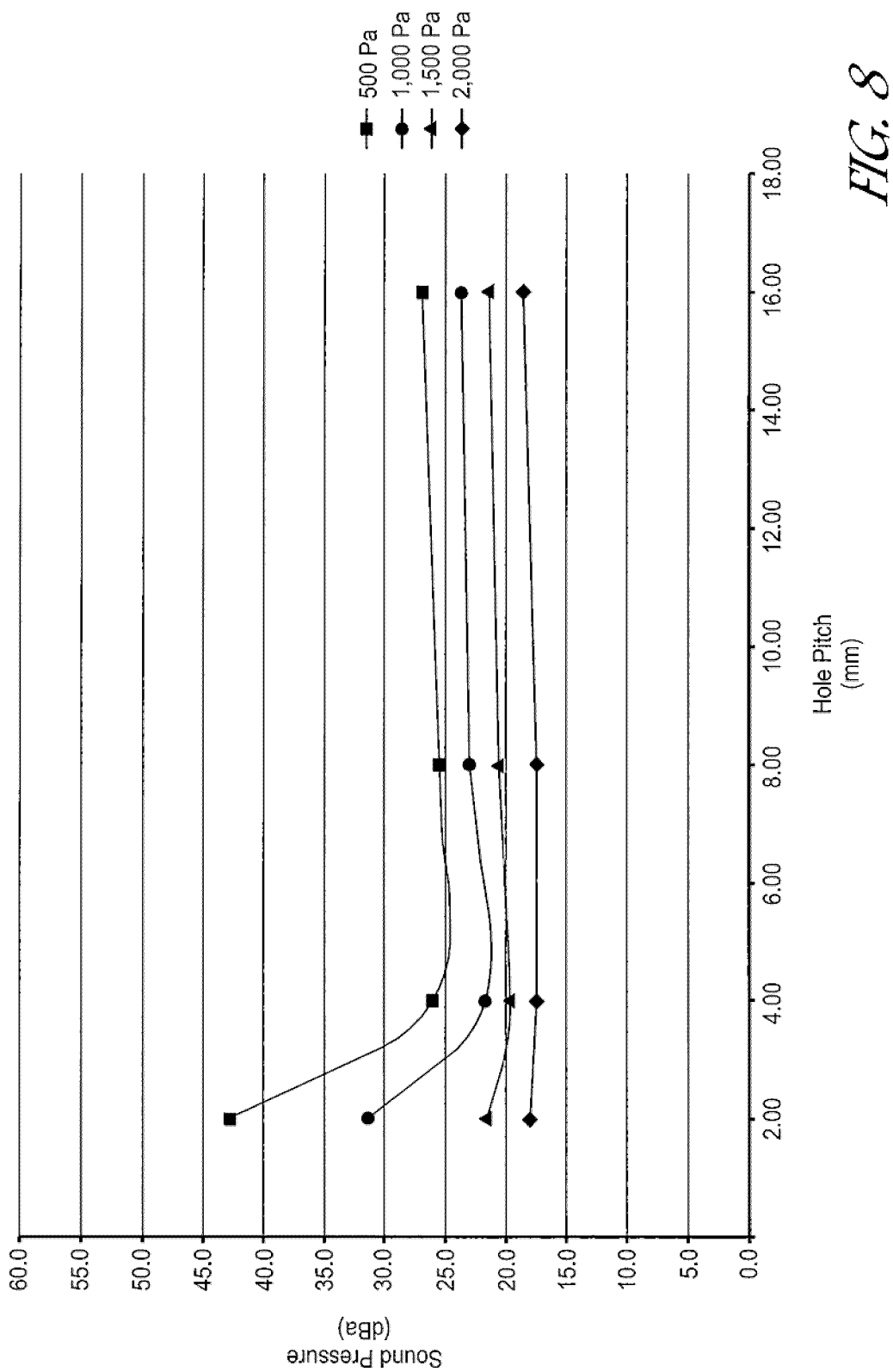
FIG. 8 is a graph showing sound pressure versus hole pitch for a 1 mm vent hole having a 0.5 mm exit radius.

FIG. 8 is a graph showing sound pressure versus hole pitch for a 1 mm vent hole having a 0.5 mm exit radius. As shown in the graph, sound levels are relatively high when the hole pitch is approximately 2. The sound levels decrease to a minimum sound level at a pitch of approximately 4. The sound levels slightly increase as the hole pitch is increased. Accordingly, a range for the hole pitch of at least approximately 4 has been found to be an acceptable range for minimizing noise levels.

The fluid flow exiting the vent holes are at a relatively high velocity, typically 20-50 m/sec. Due to conservation of energy and momentum, the exiting fluid flow entrains the surrounding environmental air. The fluid flow is at a lower pressure than the surrounding air and the pressure differential causes a portion of the surrounding environmental air to be entrained and moved along with fluid flow, which multiplies many times the effective draft from the vent holes. The experimentally determined increase of the effective draft may be in the order of 6-10 times. For example, a vent hole array with a 10 cm H2O change in pressure from the entrance to exit will create a bias flow of approximately 15-20 liters/min. The effect of the entrainment can result in approximately 90-120 liters/min of total flow being projected towards the user or bed partner. Accordingly, the ability to control the rate of entrainment can directly affect the ability to minimize the disturbance caused by the effective draft.

In some configurations, the draft and noise from the vents can be reduced or minimized by using a plenum chamber that enables the energy present in the exiting fluid flow to dissipate. The plenum chamber can enable the fluid velocity to slow and the fluid pressure to increase to reduce or prevent entrainment. The plenum chamber can have any of a plurality of different types of shapes or designs. In some configurations, the plenum chamber can be an expansion chamber that substantially reduces or prevents environmental air from being entrained, as illustrated in FIGS. 9 and 10.

Figure 9:
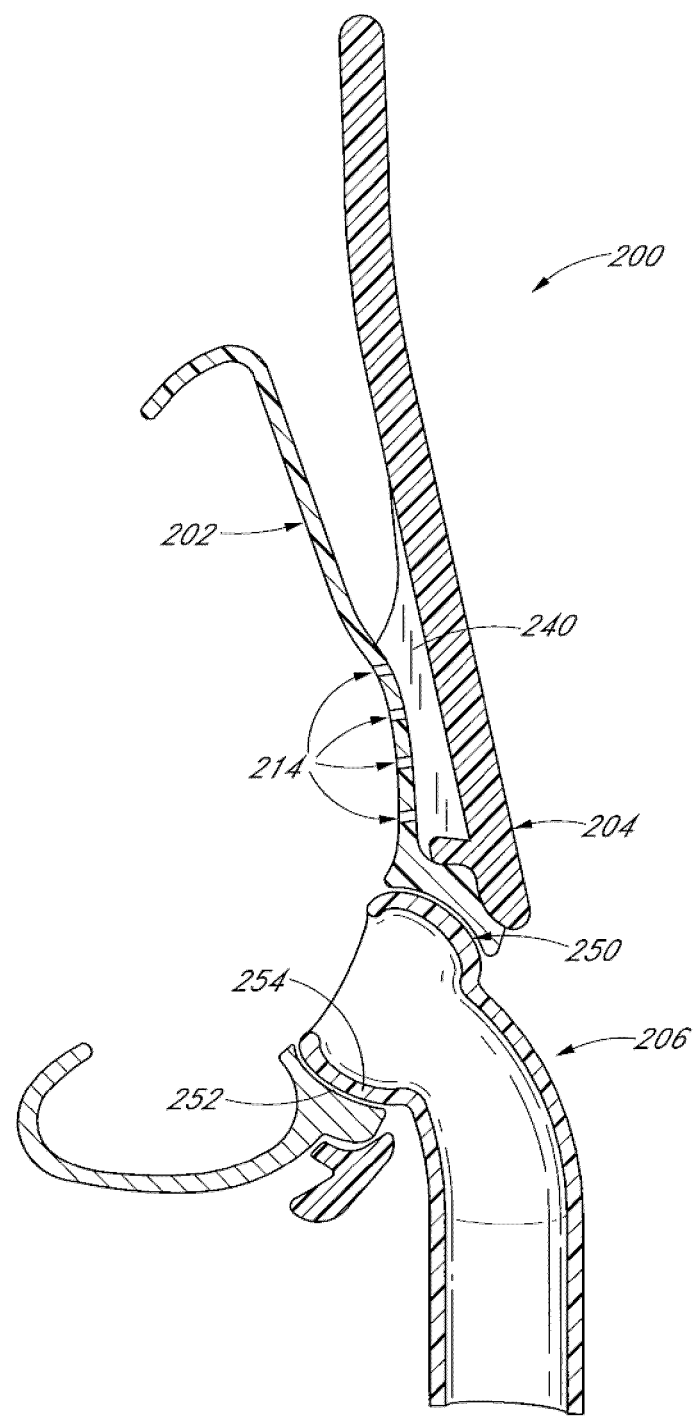
FIG. 9 is a cross-sectional view of a respiratory interface according to an embodiment of the present disclosure.

FIG. 9 illustrates a cross-section view through an interface 200 with vent holes 214 disposed in a forward-facing surface of the mask body 202 that is above the connection port assembly 206. The mask frame 204 is positioned in front of the mask body 202, such that the venting fluid flow passes through the vent holes 214 and into a plenum space 240 created between the mask body 202 and the mask frame 204. The plenum space 240 causes the fluid flow to change direction, which reduces the velocity and increases the pressure of the fluid flow. After the energy in the fluid flow is reduced, the vented fluids can exit the plenum space 240 into the environment with minimized or reduced noise levels.

Figure 10:
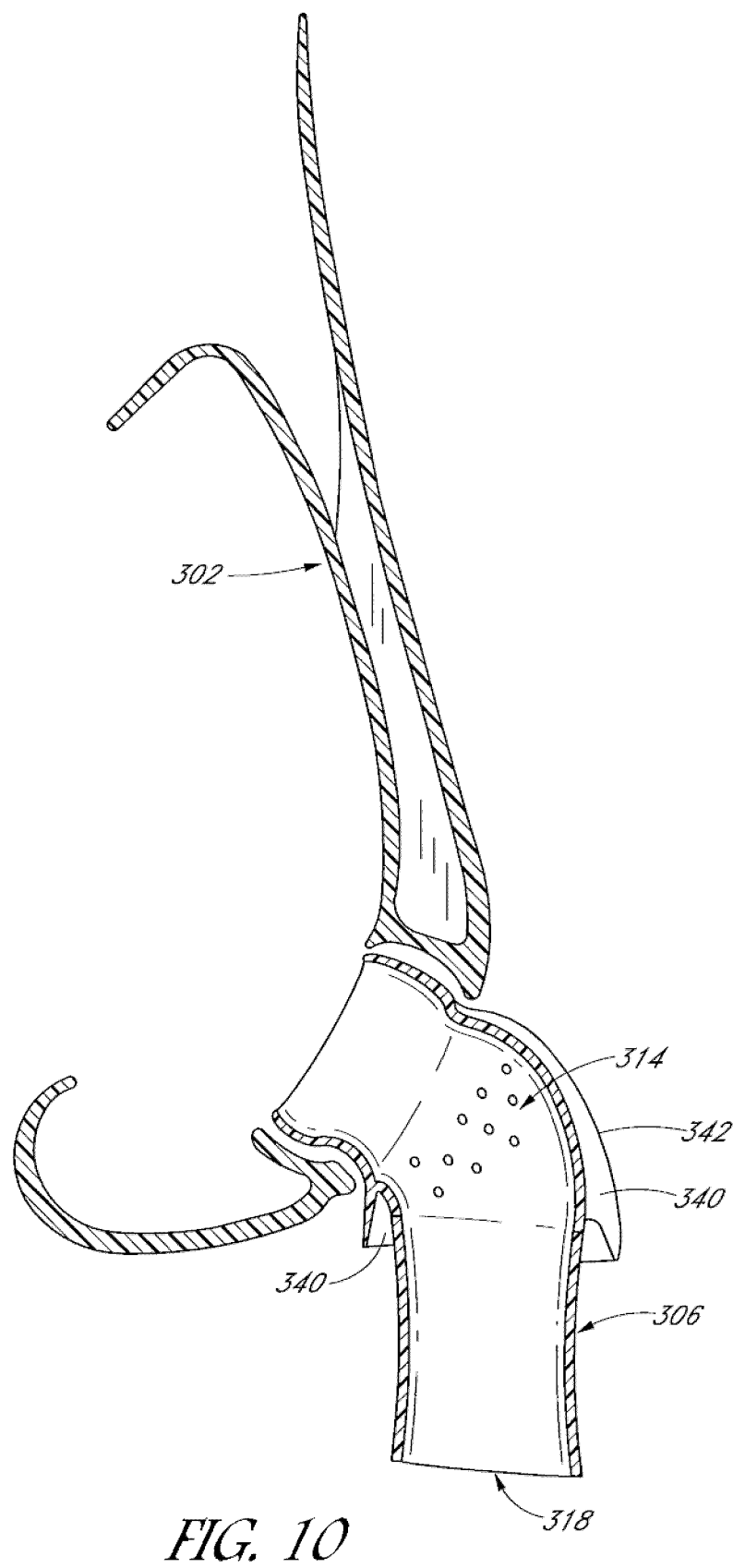
FIG. 10 is a cross-sectional view of a respiratory interface according to another embodiment of the present disclosure.

FIG. 10 illustrates a cross-sectional view of an embodiment of an interface 300 having vent holes 314 on the connection port assembly 306, disposed between the mask body 302 and the connection end 318 for the gas delivery circuit. The vent holes 314 are disposed around the entire circumference of the connection port assembly 306 in the illustrated configuration. In other configurations, the vent holes may be disposed on only a portion of the circumference, such as the front side or only half of the circumference of the connection port assembly 306. The connection port assembly 306 can have an outer shell 342 that surrounds the vent holes 314. In the illustrated embodiment, the outer shell 342 extends to cover approximately the upper half of the connection port assembly 306. In other embodiments, the outer shell can cover more or less of the connection port assembly than illustrated, but preferably covers the vent holes.

The space between the outer shell 314 and the inner surface of the connection port assembly 306 is the plenum space 340. The venting fluid passes through the vent holes 314 and into the plenum space 340, which in some configurations is designed to turn the fluid flow back on itself. The plenum space 340 reduces the velocity and increases the pressure of the fluid flow. After the energy in the fluid flow is reduced, the vented fluids can exit the plenum space 340 into the surrounding environment with minimized or reduced noise levels.

Figure 11:
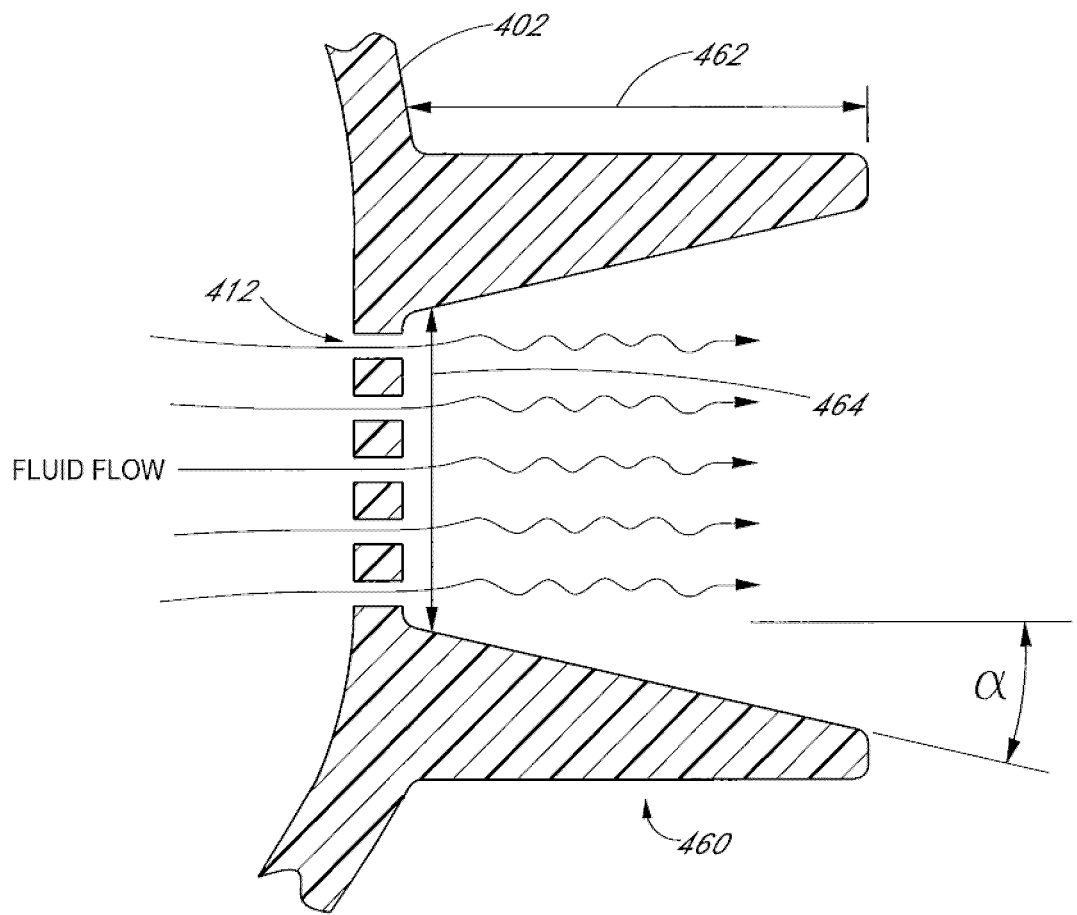
FIG. 11 is a cross-sectional view of a diffuser according to an embodiment of the present disclosure.

In some configurations, the draft and noise levels from the vents can be reduced or minimized by the application of a steadily increasing cross-sectional area, such as a diffuser 460 as illustrated in FIG. 11. FIG. 11 illustrates a cross-section of a diffuser 460 that is effective at reducing the fluid flow velocity, which reduces the draft and noise levels. The smaller end of the diffuser 460 surrounds the vents 412 and the wider end of the diffuser 460 can be open to the environment. The diffuser can have a conical shape, or other shape that has an increasing cross-sectional area. Some examples include a pyramid-shaped cone, a triangular cone and a polygonal cone.

Some geometric design considerations that can help to reduce the fluid flow velocity include the expansion angle α and the ratio of the diffuser length 462 to the root diameter 464. Diffusers with geometries similar to those described below have resulted in a reduction of the fluid flow velocity from approximately 6-8 meters per second to less than 0.8 meters per second in some embodiments.

The diffuser 460 can have an expansion angle α of at least approximately 4 degrees and/or less than or equal to approximately 8 degrees, or geometry that has the same effective cross sectional area behaviour. It has been discovered that angles greater than about 8 degrees are generally not very effective at reducing draft and noise levels in some applications. However, in some configurations, the diffuser can have an expansion angle α of at least approximately 1 degrees and/or less than or equal to approximately 15 degrees.

The length of the diffuser should be long enough to provide sufficient distance for the fluid flow velocity to decrease to a desirable level, while not protruding too much from the mask to where it causes an obstruction. For larger vents, the diffuser length can be proportionately larger to achieve the desired reduction in draft and noise levels. The ratio of the diffuser length 462 to the root diameter 464 can be at least approximately 1.4:1. In some embodiments, the ratio of the diffuser length 462 to the root diameter 464 can be at least approximately 1.25:1 and/or less than or equal to approximately 1.9:1.

Figure 12:
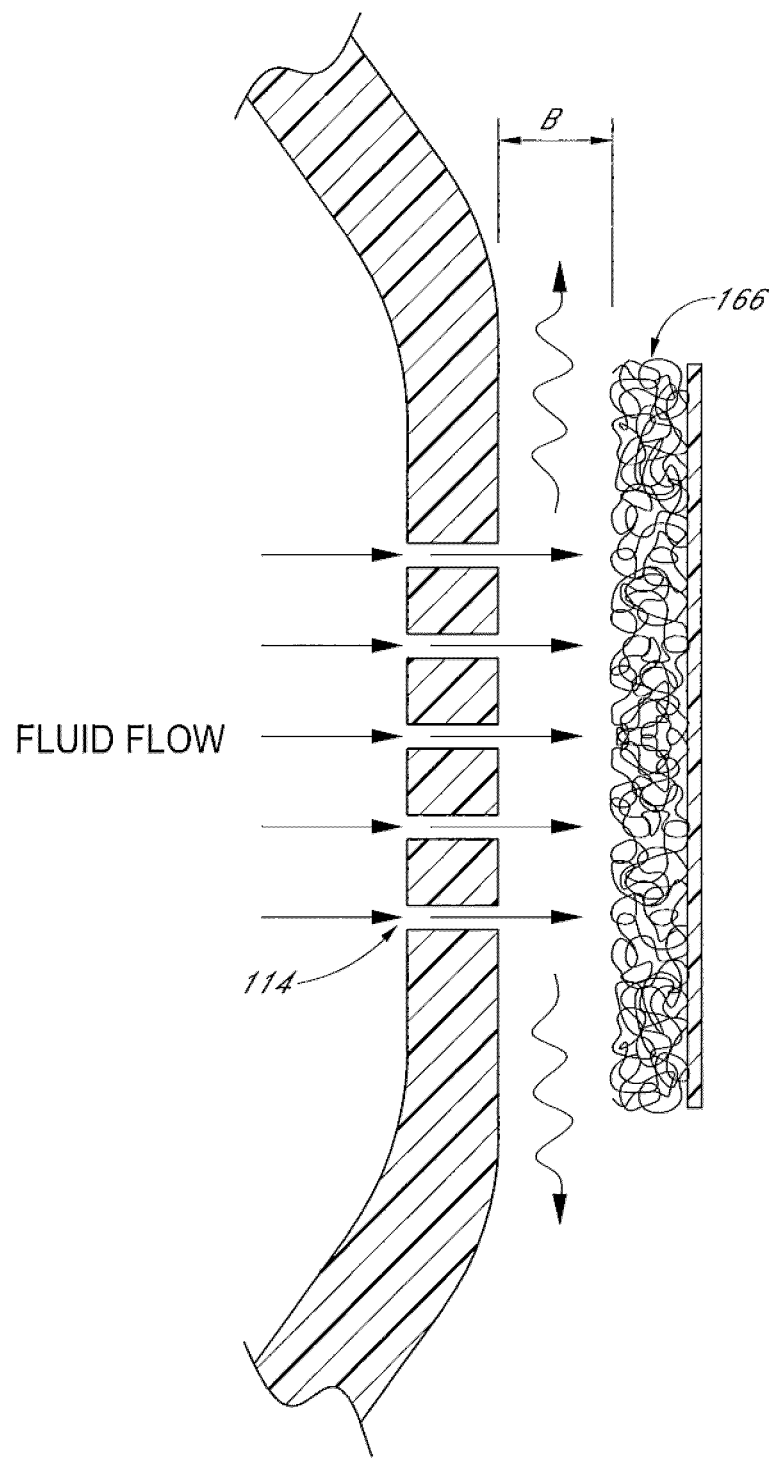
FIG. 12 is a cross-sectional view of a vent having fibrous media, according to an embodiment of the present disclosure.

With reference to FIG. 12, in some configurations, a textured or fibrous media 166 is positioned in front of the vent holes 114 such that the fluid flow exiting the vent holes impinges on the media 166. Some examples of textured or fibrous media can include wool, cotton, felt, polyester, open cell foam and the like. The media 166 helps to reduce the fluid flow velocity and diffuse the fluid flow, which reduces the draft and noise levels. The media 166 is preferably positioned between the exit of the vent holes 114 and a distance from the vent holes 114 at which the exiting fluid flow produces sound. In some configurations, the media distance β can be at least approximately 3 times the vent hole diameter and/or less than or equal to approximately 5 times the vent hole diameter. In some configurations, the media distance β can be at least approximately 1 time the vent hole diameter and/or less than or equal to approximately 10 times the vent hole diameter.

Another advantage of positioning the media 166 a distance β from the vent hole exits is that it can prevent accumulation of water around the vent holes caused from condensation of the fluid flow. The condensation can occlude the vent hole exits and undesirably increase the resistance to flow (i.e., drop in bias or leak flow rate).

Figure 13:
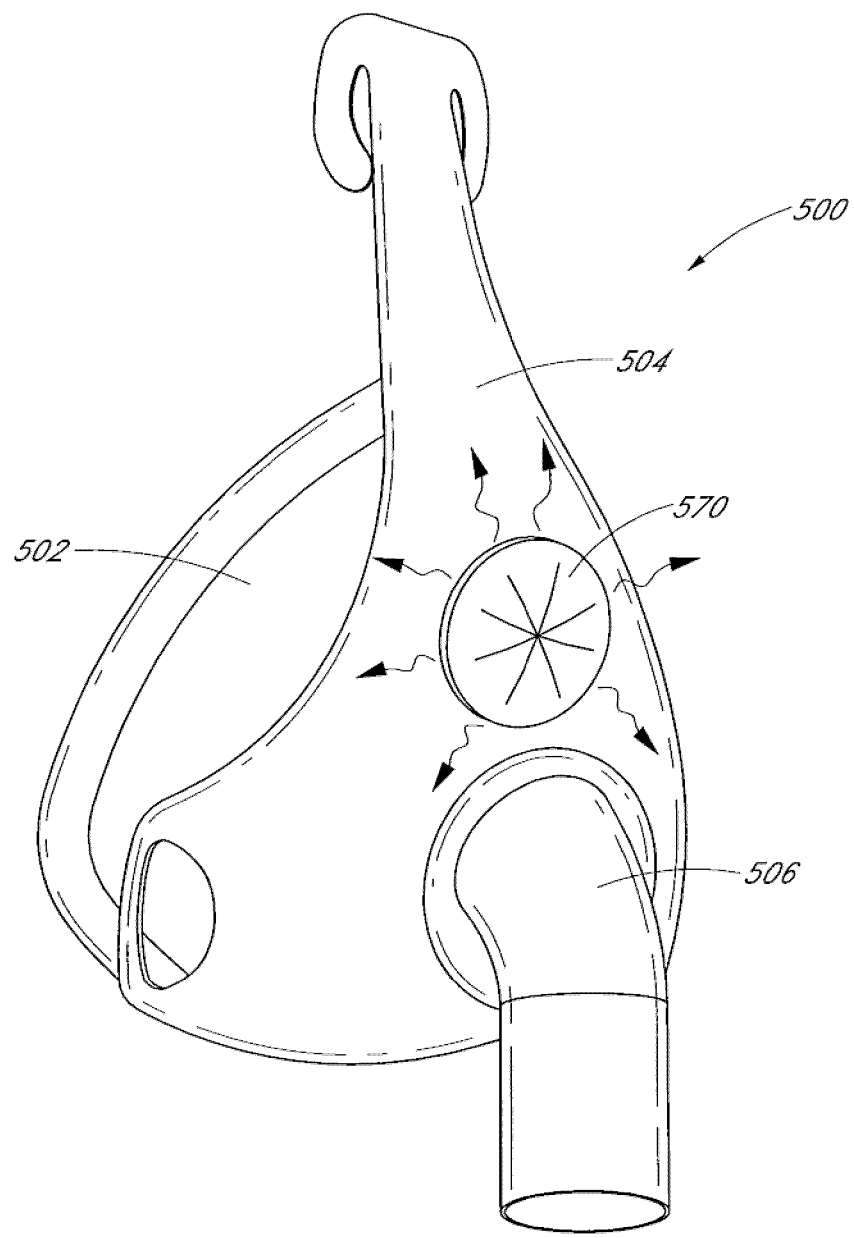
FIG. 13 is a perspective view of a respiratory interface according to another embodiment of the present disclosure.

Another vent design can include the use of an annulus configuration where the fluid flow exits through a hole or hole array and is then exhausted radially outward by an annulus cap that redirects the fluid flow through a plenum space and eventually vents to environment. In some configurations, the plenum chamber can redirect the gas flow through an angle of between 45 degrees and about 135 degrees. FIG. 13 illustrates an embodiment of an interface 500 with an annulus cap 570 that vents the fluid flow radially outward, reducing the fluid flow velocity, the draft and noise levels. In the illustrated embodiment, the annulus cap 570 is located on the mask frame 504 above the connection port assembly 506. In some embodiments, the annulus cap can be disposed on the mask body 502 or the connection port assembly 506 instead of or in addition to the mask frame 504.

Figure 14:
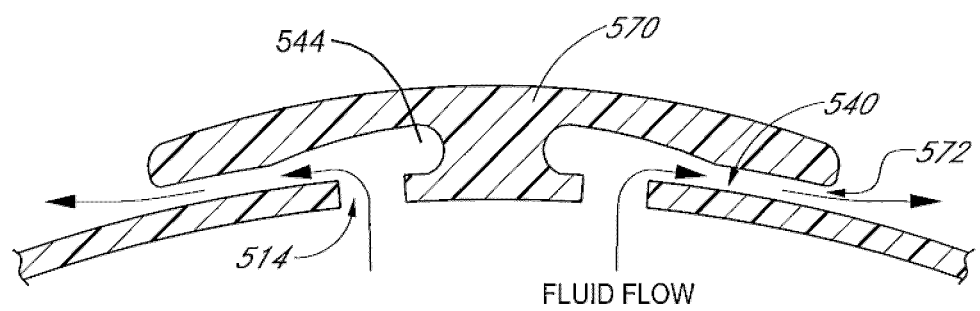
FIG. 14 is a cross-sectional view of an annulus cap according to an embodiment of the present disclosure.

FIG. 14 illustrates a cross-section of an annulus cap 570 showing the fluid flow through the cap. The annulus cap 570 covers vent holes 514 that are in fluid communication with the inside of the mask body. The fluids can flow through the vent holes 514 and are directed through a plenum space 540. The direction of the fluid flow is also redirected to exhaust radially outward. As described previously, the fluids flow through the vent holes 514 at a relative high velocity and low pressure. As the fluids enter the plenum space 540, they are redirected by the walls of the annulus cap 570, which reduces the fluid flow velocity and increases the fluid pressure. The fluids flow through the plenum space 540 and exit to the environment in a radial direction. The annulus cap 570 reduces or minimises the sound creation from the fluid flow.

In the illustrated configuration, the annulus cap 570 is integrally formed with one of the interface components, such as the mask body, mask frame or connection port assembly. In some configurations, the annulus cap can be a separate component that is fastened over the top of the vents with a functional coupler, such as threaded fasteners, clips or an interference fit.

There are a number of geometric factors that influence the amount of sound energy created by the vortex shedding as the fluid flow exits the annulus cap. These factors can include: (1) the cross-sectional area of the plenum space 540, which affects the fluid velocity exiting the slot; (2) the profile of the plenum space 540, which also affects the fluid velocity exiting the slot; and (3) the exit radii 572 of the annulus cap 570 surrounding the plenum space exit, which influences the location and resulting sound level of the vortex shedding that occurs in the existing fluid flow. Similar to as discussed above, a given flow volume will have a greater velocity through a relatively smaller cross-sectional area compared to a relatively larger cross-sectional area. Higher flow velocities can produce more draft and sound levels.

The profile of the plenum space 540 can be configured to slow down the fluid velocity and help reduce noise levels. For example, in the configurations illustrated in FIGS. 14 and 15, the plenum space 540 includes pockets 544 adjacent the outlet side of the vent hole 514. When the fluid flow enters the pocket 544, it can create turbulence that slow down the fluid flow, which can help reduce noise levels of the fluid flow exiting the annulus cap.

Similar to as discussed above, the fluid flow exiting the annulus cap 570 are at a relatively high velocity. Due to conservation of energy and momentum, the exiting fluid flow entrains the surrounding environmental air. The fluid flow is at a lower pressure than the surrounding air and the pressure differential causes a portion of the surrounding environmental air to be entrained and moved along with fluid flow, which multiplies many times the effective draft from the vent holes. The ability to control the rate of entrainment can directly affect the ability to minimize the disturbance caused by the effective draft.

Figure 15:
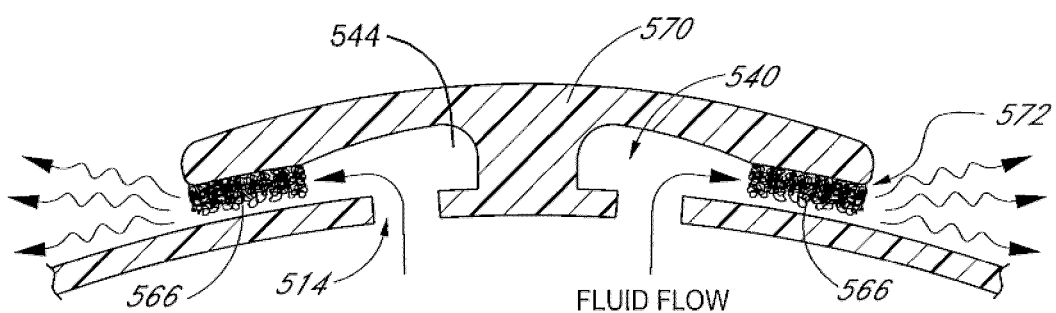
FIG. 15 is a cross-sectional view of an annulus cap with fibrous media according to an embodiment of the present disclosure.

In some configurations, the rate of entrainment can be reduced by the use of a fibrous media 566 positioned in the flow path, as illustrated in FIG. 15. In the illustrated configuration, the fibrous media 566 is toward the exit of the plenum space 540. In other configurations, the fibrous media 566 can be positioned anywhere along the flow path through the annulus cap 570. The fibrous media 566 can provide a tortuous path for the fluid flow to pass through, which produces friction and reduces the fluid velocity. The fluid velocity can be reduced to a level of sufficiently low energy that the velocity difference between the fluid flow exiting the annulus cap 570 and the surrounding air is at a point that there is minimal or reduced entrainment of the surrounding air.

Instead of or in addition to having vents on the mask body or mask frame, the bias flow can be incorporated into the leak rate that normally occurs through a ball joint or swiveling joints present in some interfaces. Some interfaces have either a ball joint or a swivel joint to help reduce or minimize the effect of torque that the delivery tube may induce on the interface and user. These joints provide free motion with low or minimal leak rate. The descriptions below relate to an interface having a ball joint. However, it should be understood that the same design concepts can be applied to swivel joints.

In some configurations, the connection port assembly 206 can be connected to the mask body 202 with a ball joint 250, as illustrated in FIG. 9. In some configurations, the connection port assembly 206 can be connected to the mask frame 204 instead of or in addition to the mask body 202. In the illustrated configuration, the mask body 202 has a ball socket 252 with a concave surface configuration that can receive a ball end 254 of a connection port assembly 206. The ball end 254 has an outer surface that is contoured to be snap fit into the ball socket 252. The ball joint 250 can allow the surfaces to slide relatively freely with each other such that the angle between the connection port assembly 206 and mask body 202 can be easily changed.

Figure 16:
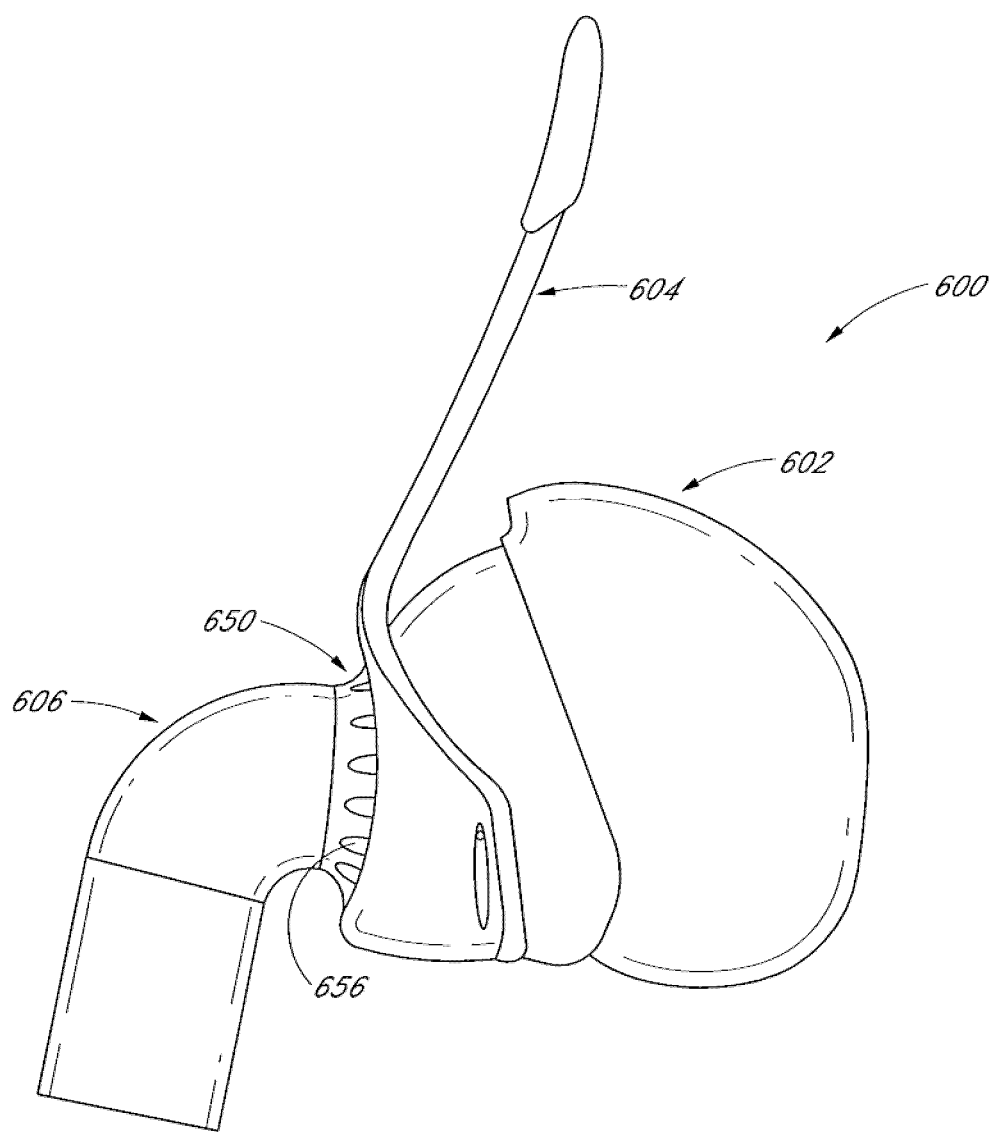
FIG. 16 is a side view of a respiratory interface according to another embodiment of the present disclosure.

There are several options for the geometry of the gas path through a ball joint or swivel joint that can produce a stable, predictable leak. With reference to FIG. 16, an interface 600 is shown having a ball joint 650 between the connection port assembly 606 and mask body 602. The ball joint 650 includes grooves 656 that allow the fluids in the mask to exhaust to the environment in a controlled, predictable manner. The quantity and cross-sectional area of the grooves 656 can affect the flow rate of fluids venting through the ball joint.

Figure 17:
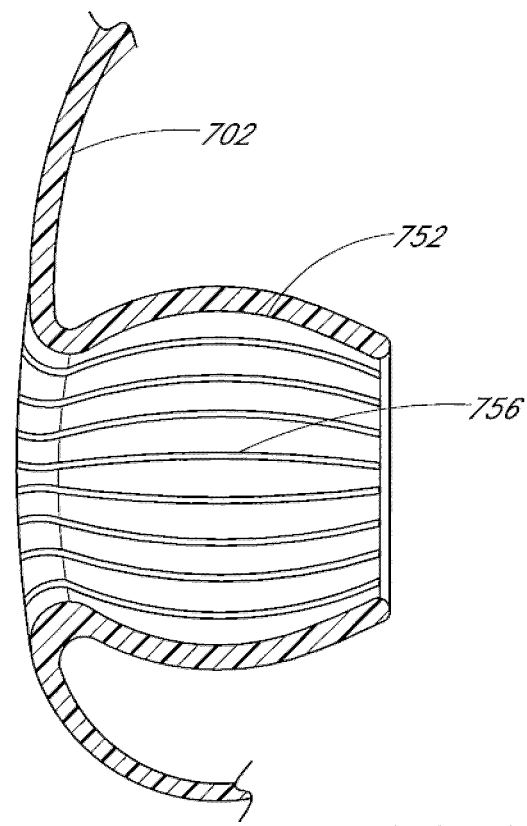
FIG. 17 is a cross-sectional view of a ball socket with grooves according to an embodiment of the present disclosure.
Figure 18:
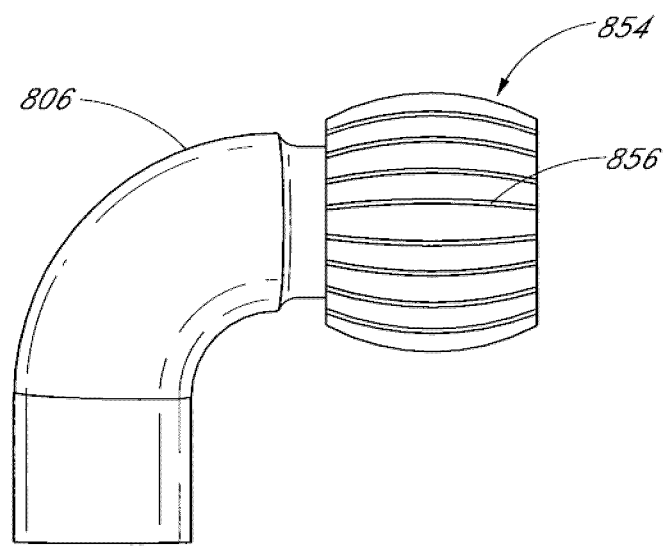
FIG. 18 is a side view of a connection port assembly with a ball end having grooves according to an embodiment of the present disclosure.

The grooves can be disposed on either or both components of the ball joint. For the example, FIG. 17 illustrates grooves 756 on the interior surface of the ball socket 752. The ball socket 752 can be a part of the mask body 702, as illustrated, or the mask frame. In some configurations, the grooves 856 can be disposed on the exterior surface of the ball end 854 of the connection port assembly 806, as illustrated in FIG. 18. The grooves provide fluid communication between the inside of the mask to the environment while also providing a mechanism to reduce the friction between the ball and the socket. The reduced friction is advantageous for further reducing the effect of tube torque on the interface.

Preferably, the ball joint can provide a consistent, reliable leak rate independent of the orientation of the ball socket. The cross-sectional areas of each groove can be substantially the same so that the leak rate is the substantially the same no matter which orientation the ball socket is in.

Figure 19:
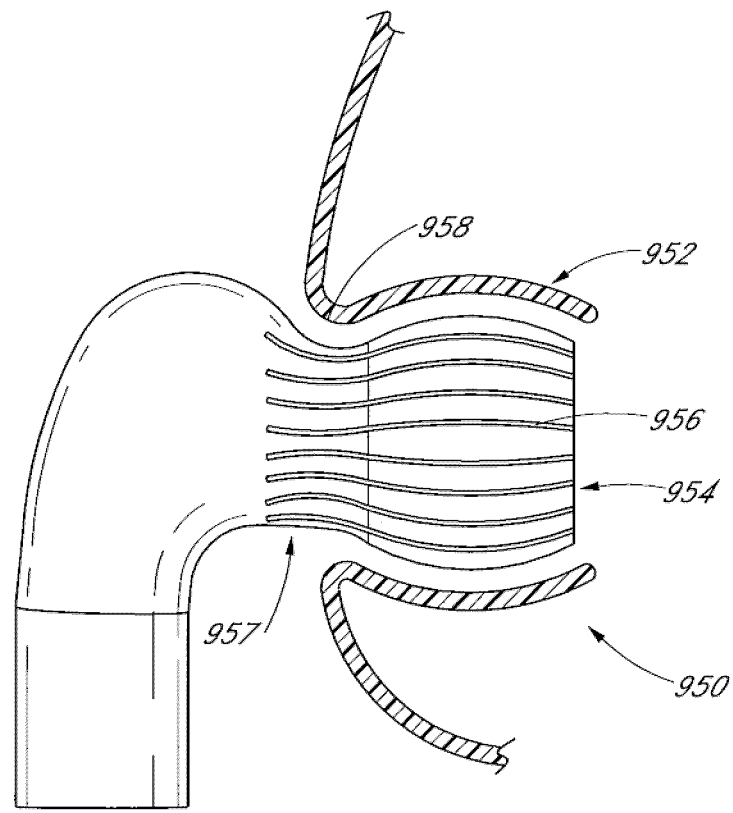
FIG. 19 is a cross-sectional view of a ball joint according to an embodiment of the present disclosure.

In addition, the ball joint can be designed to minimize the obstruction of the air pathway as the fluids exit the joint. If there are obstructions in the fluid pathway, the sound levels may change as the ball joint is moved, especially when flexed to its extremes. For example, FIG. 19 illustrates a ball joint 950 with a ball socket 952 and ball end 952. The grooves 956 are disposed on the outer surface of the ball end 952 and extend to or beyond the neck 957 of the ball end. Because the grooves 956 extend to or beyond the neck 957, the socket edge 958 does not occlude the flow path of the exhaust fluid when the ball joint is flexed to its extremes, which can lead to unstable flow rates and noise level changes.

Figure 20:
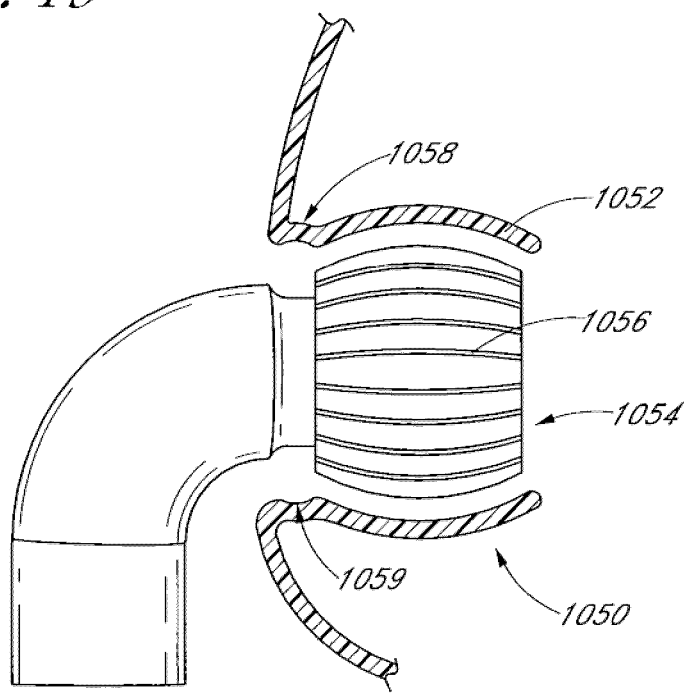
FIG. 20 is a cross-sectional view of a ball joint according to another embodiment of the present disclosure.

FIG. 20 illustrates a configuration of a ball joint 1050 having a gutter 1059 on the socket edge 1058. The ball joint 1050 has a ball socket 1052 and ball end 1054, with grooves 1056 disposed on the ball end 1054. Instead of the grooves 1056 extending to the neck of the ball end to help prevent occlusion of the fluid flow, the illustrated gutter 1059 provides clearance for a fluid pathway when the ball joint is flexed to its extremes.

In some embodiments, the interface can have a separate ball socket component that can be separately made and coupled to the mask body or mask frame. A separate ball socket component can advantageously allow improved manufacturing and product quality. The small and detailed features, such as the grooves, can be better controlled and the part tolerances can be better controlled and result in more consistent dimensions having a more consistent flow rate performance. Moulding a separate ball socket component may also allow for production of more complex groove designs as a result of not having to accommodate undercuts and other geometric restrictions of other components. The ball socket component can be attached to the mask body or mask frame through any type of functional coupling, such as overmoulding, adhesives, clips, welding and interference fit.

Figure 21A:
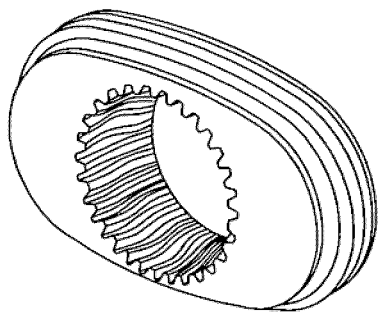
FIGS. 21A-L are perspective views of ball socket components with groove patterns, according to various embodiments of the present disclosure.
Figure 21B:
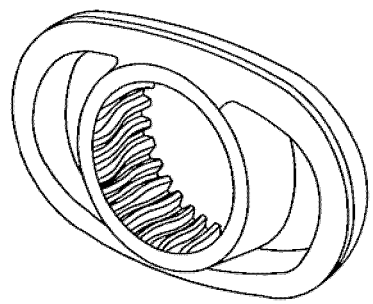
Figure 21C:
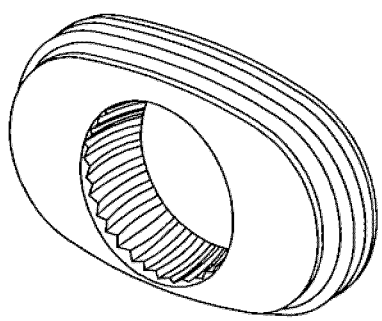
Figure 21D:
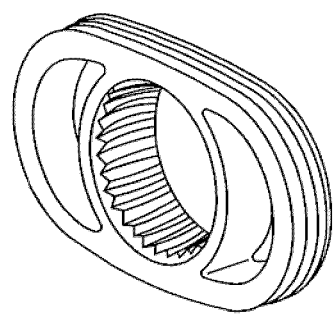
Figure 21E:
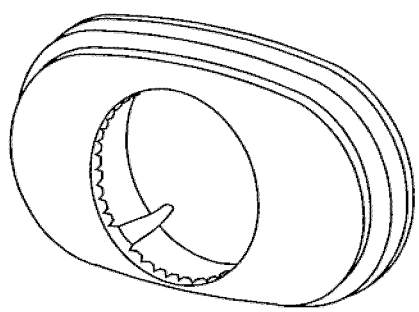
Figure 21F:
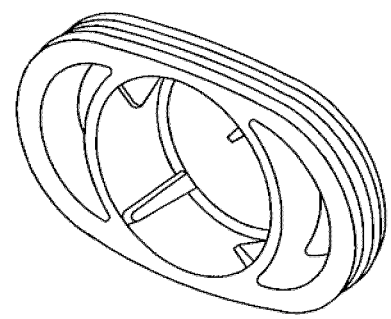
Figure 21G:
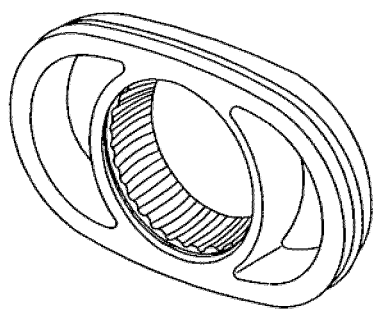
Figure 21H:
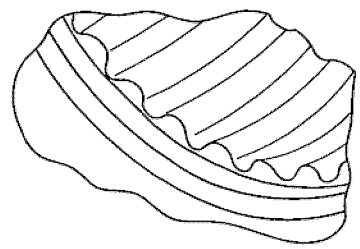
Figure 21I:
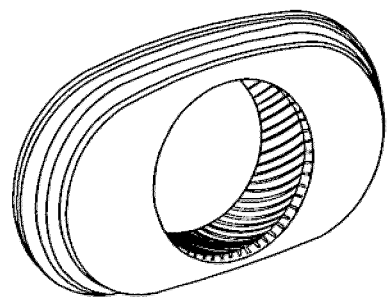
Figure 21J:
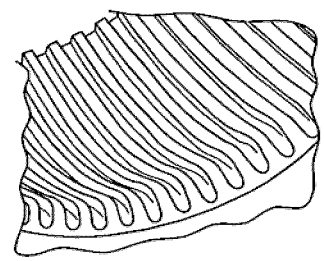
Figure 21K:
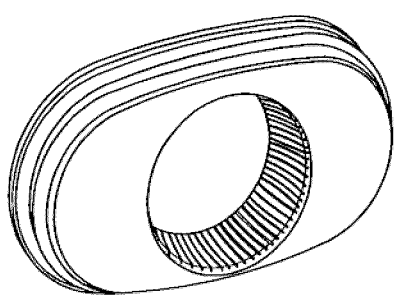
Figure 21L:
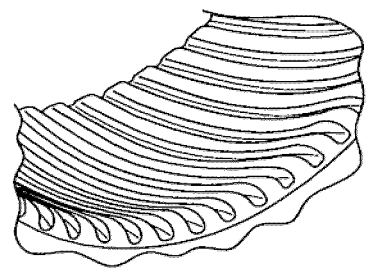

FIGS. 21A-L illustrate some examples of ball socket components with some possible groove patterns for the ball joint. FIGS. 21A-B illustrate front and rear perspective views, respectively, of a groove pattern. FIGS. 21C-D illustrate front and rear perspective views, respectively, of another groove pattern. FIGS. 21E-F illustrate front and rear perspective views, respectively, of a groove pattern having four large grooves. FIGS. 21G-F illustrate a front perspective and close-up view of another embodiment of a ball socket component with a groove pattern. FIG. 21I-J illustrate a front perspective and close-up view of a groove pattern with a 30 degree twist. FIGS. 21K-L illustrate a front perspective and close-up view of a groove pattern with an increased number of grooves, 75 grooves in the illustrated embodiment.

FIGS. 22A-C illustrate a ball socket component 1151 having a plenum space 1140. The ball socket component 1151 has a ball socket 1152 for accepting a ball end. In some configurations, the ball socket can be smooth or have grooves, as discussed above. The rear side of the ball socket component 1151 can have vent holes 1114 and the front side can have slots 1115. In some configurations, the front side may have openings in other shapes other than slits as shown in the illustrated embodiment. Between the vent holes 1114 and slots 1115 can be a plenum space 1140 that reduces the fluid flow velocity, and reduces the draft and noise levels.

Figure 23:
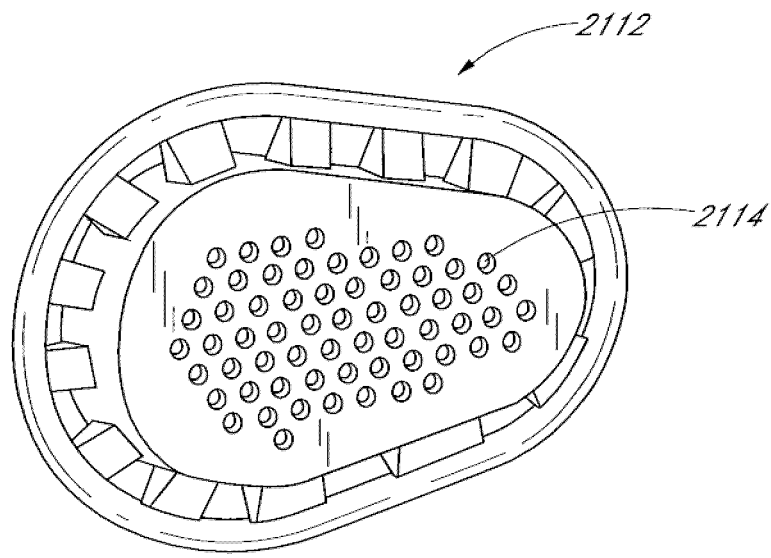
FIG. 23 is a perspective view of a vent module, according to an embodiment of the present disclosure.

In some configurations, the vent holes can be disposed on a separate insert that is coupled to the interface. FIG. 23 illustrates an example of a vent module 2112 having a plurality of vent holes 2114. The separate vent module 2112 advantageously allows improved manufacturing and product quality. By having the vent holes 2114 in a separate component the moulding of the small and detailed vent apertures can be better controlled, and the part tolerances can be better controlled and result in more consistent hole dimensions having a more consistent flow rate performance. Moulding a separate vent module 2112 may also allow for production of more complex vent designs as a result of not having to accommodate undercuts and other geometric restrictions of other components, such as the mask body for example.

Improved control of the part dimensions may also improve control of noise levels, such as by controlling the hole contours to produce a smooth air flow through the holes.

Figure 24:
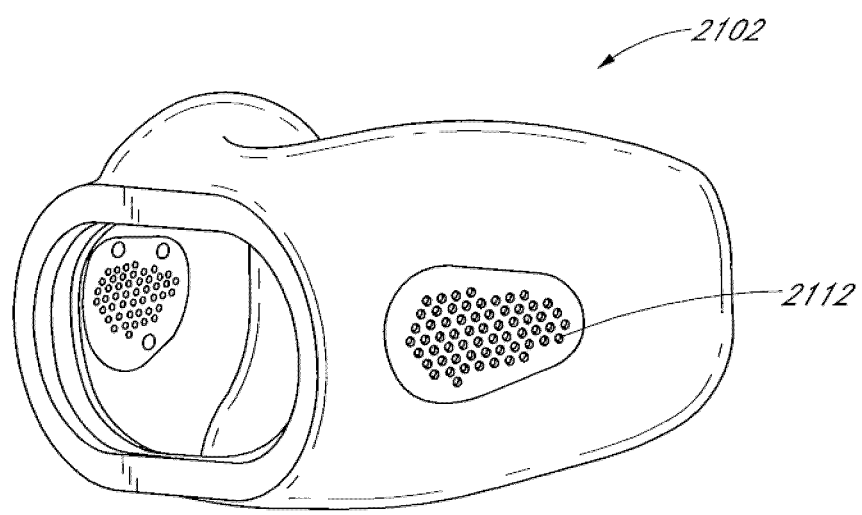
FIG. 24 is a perspective view of an interface with the vent module of FIG. 23.
Figure 25:
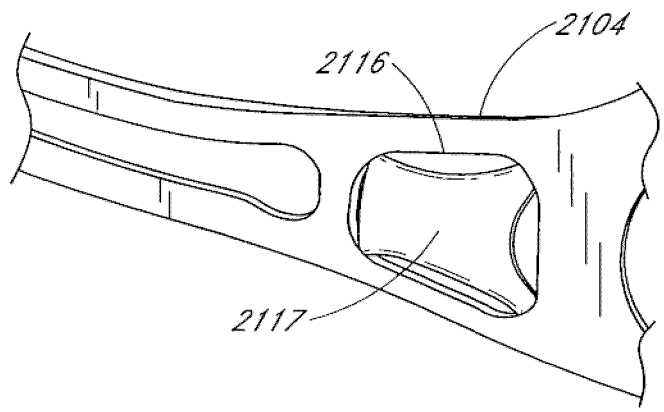
FIG. 25 is a perspective view of a mask frame, according to an embodiment of the present disclosure.
Figure 26:
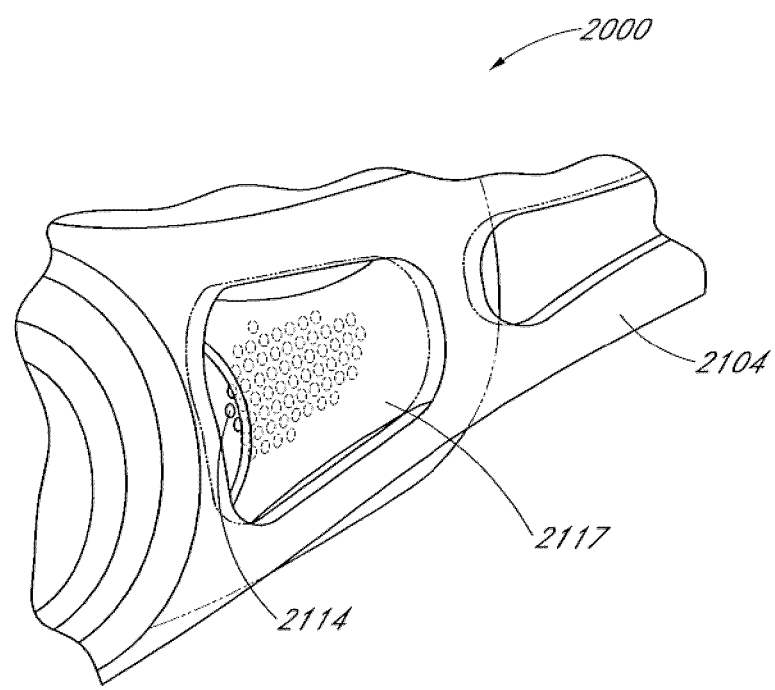
FIG. 26 is a perspective view of the interface of FIG. 24 and the mask frame of FIG. 25.

FIG. 24 illustrates the vent module 2112 coupled to a mask body 2102. The vent module 2112 can be attached to the mask body 2102 or mask frame through any type of functional coupling, such as overmoulding, adhesives, clips, welding and interference fit. With reference to FIGS. 25 and 26, a mask frame 2104 can be coupled to the mask body 2102. The mask frame 2104 can have a cutout 2116 that is configured to be positioned over the vent module 2112. In some configurations, a vent cover 2117 can be disposed across the cutout 2116 to reduce the draft from the vent holes 2114. The space between the vent module 2112 and the vent cover 2117 can act as a plenum space to reduce the fluid flow velocity, and reduce the draft and noise levels.

Figure 27:
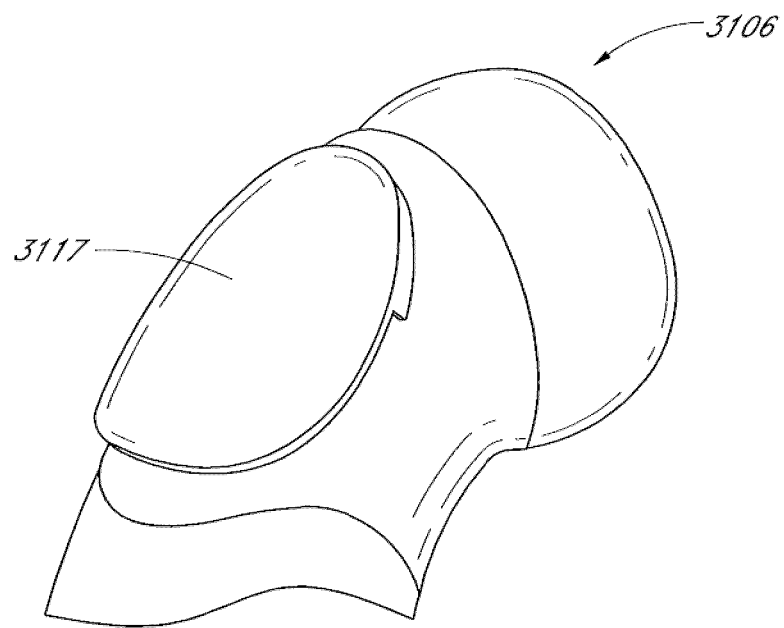
FIG. 27 is a perspective view of a connection port assembly having a vent, according to an embodiment of the present disclosure.
Figure 28:
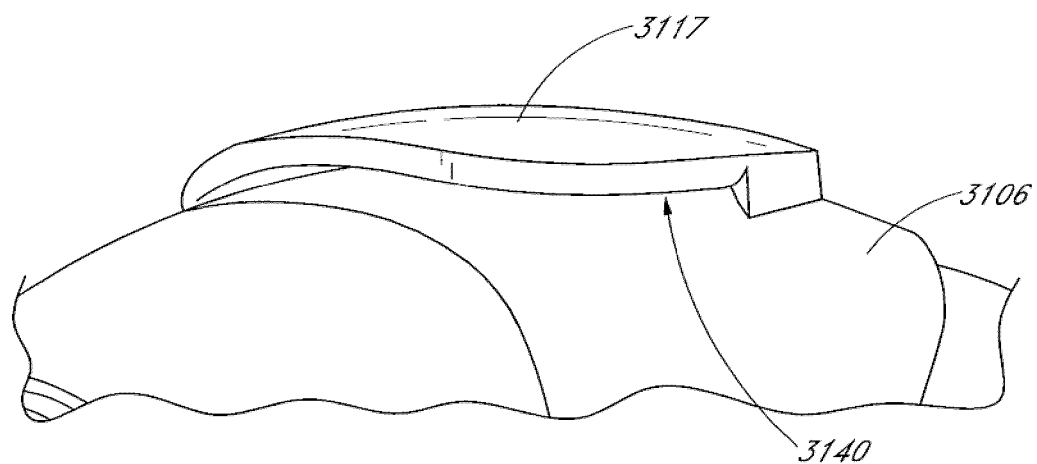
FIG. 28 is a close-up perspective view of the vent of FIG. 27.
Figure 29:
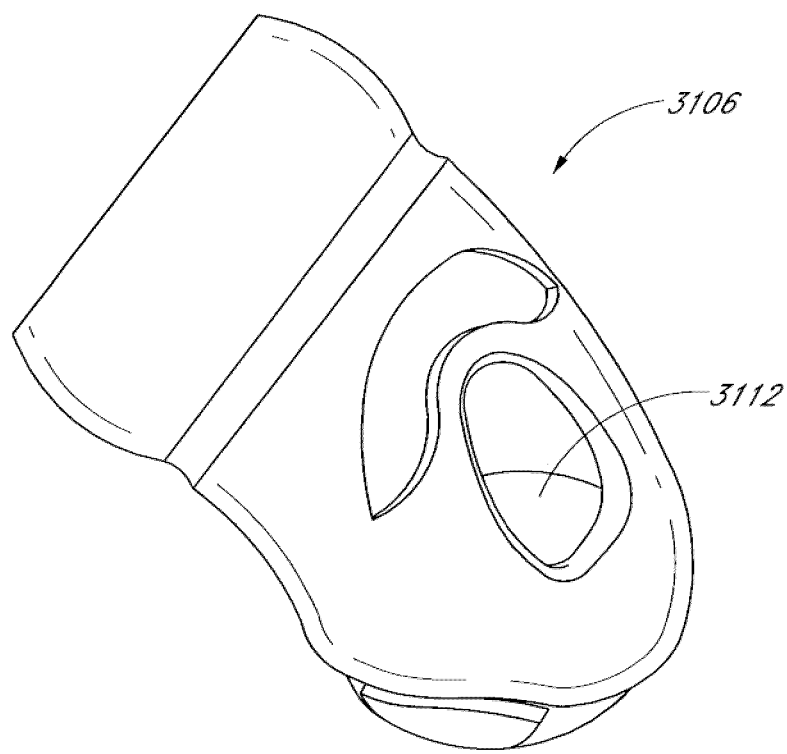
FIG. 29 is a perspective view of the connection port assembly of FIG. 27 without the vent cover.
Figure 30:
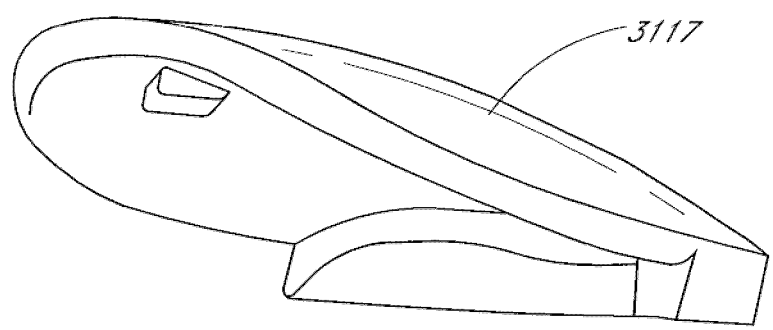
FIG. 30 is a perspective view of the vent cover of FIG. 27.

FIGS. 27 and 28 illustrate an embodiment of a connection port assembly 3106 having a vent 3112 with a vent cover 3117. The vent 3112 can be a single opening through the wall of the connection port assembly 3106, as illustrated in FIG. 29, or can be a plurality of holes or slots, as discussed previously. FIG. 30 illustrates the vent cover 3117, which can be a separate component that is coupled to the connection port assembly 3106 through any type of functional coupling, such as overmoulding, adhesives, welding, clips and interference fit. In some embodiments, the vent cover is integrally formed or moulded with the connection port assembly.

The vent cover 3117 can help to reduce the draft from the vent 3112. The plenum space 3140 between the connection port assembly 3106 and the vent cover 3117 can help reduce the fluid flow velocity, and reduce the draft and noise levels as discussed previously.

As mentioned above, having vent holes in a radial configuration, such as around a cylinder, is beneficial in reducing or minimizing the amount of draft that is felt by the user or bed partner. However, moulding radial holes, or holes on a curved surface, can be difficult from a process point of view. Accordingly, in some configurations, the vent holes can be formed on a vent module made of soft material and then attached to the interface. The soft material can allow for the vent module to be wrapped around or contoured onto the interface. In some configurations, the soft material of the vent module can be rubber, plastic, silicone or any other suitably flexible material. In some embodiments, however, the material can be a harder material and can have some functional means of being bent, such as with hinges or reliefs that promote bending.

Figure 31A:
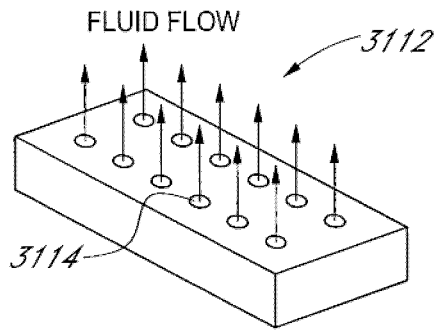
FIG. 31A is a perspective view of a vent module, according to an embodiment of the present disclosure.
Figure 31B:
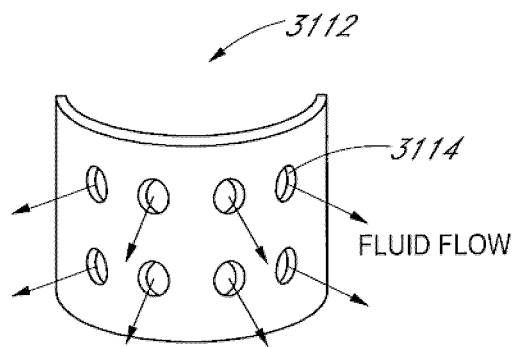
FIG. 31B is a perspective view of the vent module of FIG. 31A, in a curved configuration.
Figure 31C:
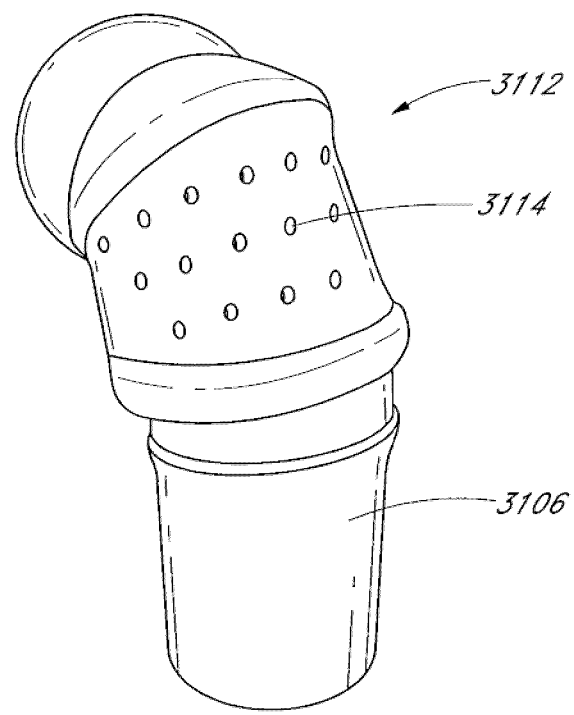
FIG. 31C is a perspective view of the vent module of FIG. 31A attached to a connection port assembly.

FIG. 31A illustrates a vent module 3112 that is moulded from a flat piece of material. As illustrated, the fluid flows in generally the same direction as it flows out of the vent holes 3114. FIG. 31B illustrates the vent module 3112 in a curved configuration. The vent holes 3114 are in a radial pattern and the fluid flows from the vent holes 3114 in divergent directions. In other words, when the vent module is curved, there are no two columns of holes at the same angle. This makes it harder for the fluid flow to entrain air and therefore reduces the draft effect, which can reduce the noise level as well. FIG. 31C illustrates the vent module 3112 coupled to a connection port assembly 3106. The vent module 3112 can be overmoulded with the interface or attached by other means, such as for example adhesives or welding.

Figure 32B:
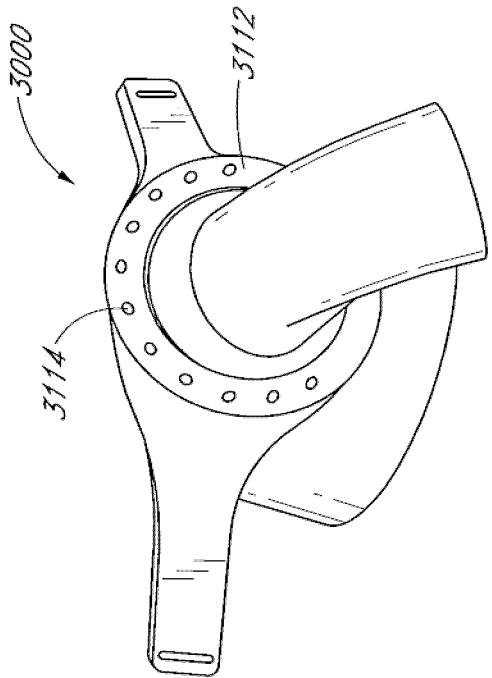
FIG. 32A-E are perspective view of bendable vent modules, according to various embodiments of the present disclosure.
Figure 32D:
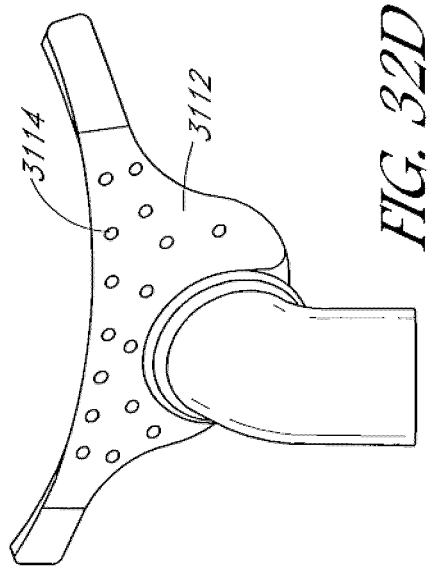
Figure 32A:
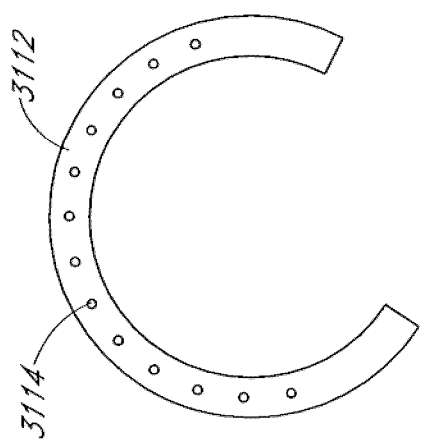

FIGS. 32A-E illustrate various examples of a vent module that is bent and attached to different portions of interfaces. FIG. 32A illustrates a flat circular vent module 3112 that can be curved into a frustoconical shape and attached to the interface 3000. In the illustrated configuration of FIG. 32B, the vent module 3112 is disposed around the ball joint. The vent holes 3114 are pointed in a divergent direction relative to the centre of the circular vent module 3112, which helps diffuse the fluid flow and reduce draft.

Figure 32C:
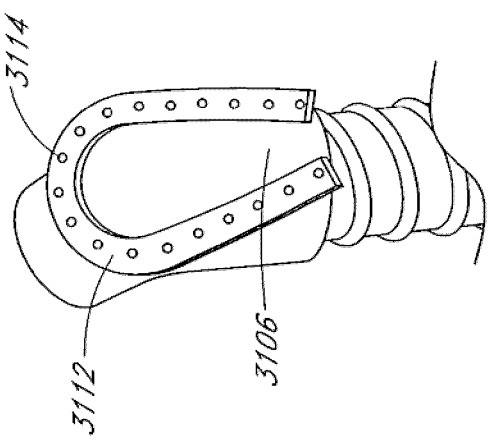
Figure 32E:
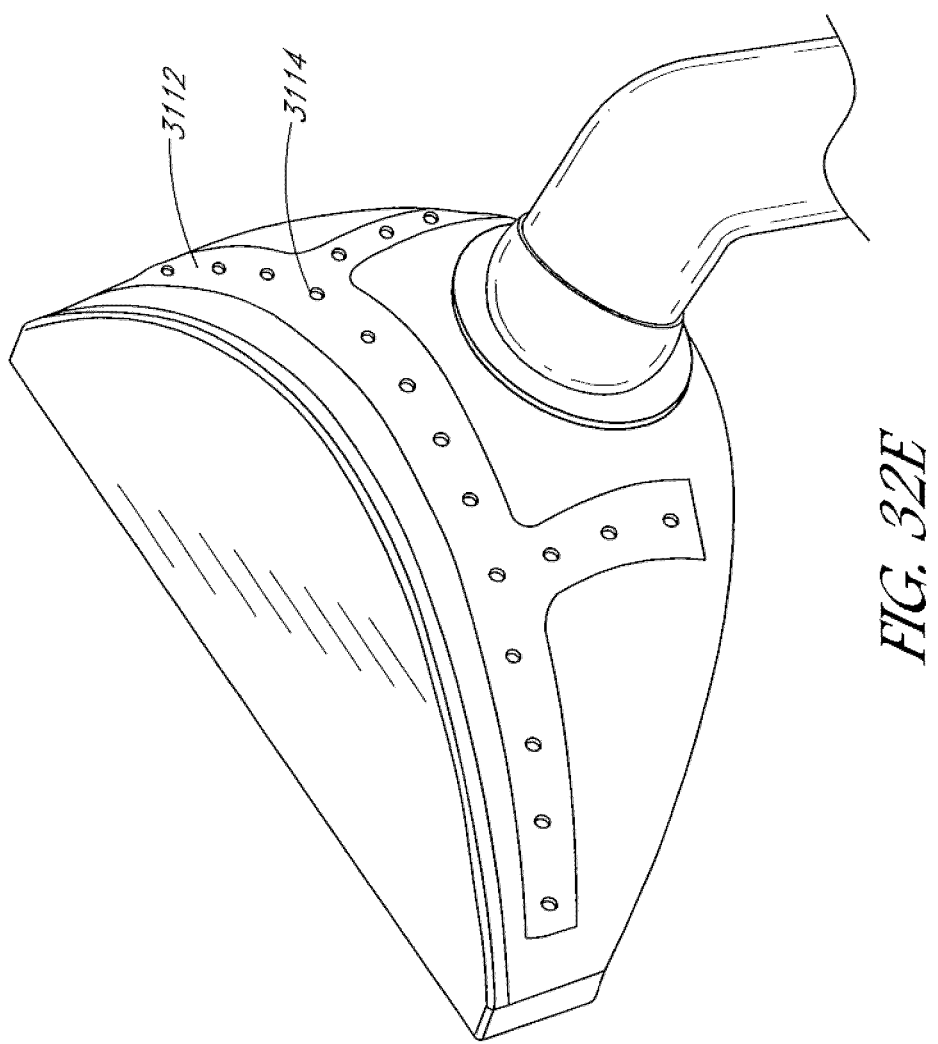

FIG. 32C illustrates a horseshoe-shaped vent module 3112 that can fit around the contours of the connection port assembly. FIG. 32D illustrates a vent module 3112 that can cover the front portion of the mask. In this configuration, the large surface area of the front portion can be used for vent holes 3114, allowing for a large venting flow rate. FIG. 32E illustrates another embodiment of a vent module 3112 that is configured to fit across the front portion of the interface. In the illustrated embodiment, the vent module 3112 includes strips with vent holes 3114 that extend around the ball joint.

It has been discovered that instead of vent holes, slots can be used to vent the fluids. Slots have some advantages over vent holes, which may include more venting flow rate, better manufacturability and lower noise levels. The slots may produce less noise compared to holes because the slots have less surface structures for the fluid to flow past, which is a contributor to noise production.

FIG. 33A illustrates an exploded view of an interface 4000 having slots 4114 for venting. The slots 4114 can be disposed on a vent module 4112 and a slot cover 4115 can be positioned over the vent module 4112 to form a flow path through the slots 4114, as illustrated in FIG. 33B. In the illustrated embodiment, the slot cover 4115 includes the ball socket 4152 such that the connection port assembly 4106 can connect to the slot cover 4115.

With continued reference to FIG. 33A, the vent module 4112 can have an inner radius 4113, which can help provide a smoother flow path through the slot and help reduce noise levels. It has been discovered that placing a tab 4117 at the exit of the slots 4114 can help to reduce noise levels. In experimentation, an optimal tab 4117 length was found to be approximately 2 mm long. However, in some embodiments, the tab length can be any length that provides suitable noise reduction. The illustrated configuration has 4 slots spaced equal distances apart. In some configurations, the number of slots can be at least 1 and/or less than or equal to 8 slots. Furthermore, with reference to FIG. 33B, the exhausting fluid flow is shown flowing radially outward from the interface. In other configurations, the exhaust can be directed in any suitable direction to control the draft from the fluid flow.

FIGS. 34A-B illustrate another configuration having two slots 5114. The vent module 5112 of this interface 5000 has two slots 5114 about 180 degrees apart. The slot cover 5115 fits over the vent module 5112, forming the flow path through the slots 5114. This configuration also shows a connection port assembly 5106 that is configured to connect with the slot cover 5115.

Figure 35A:
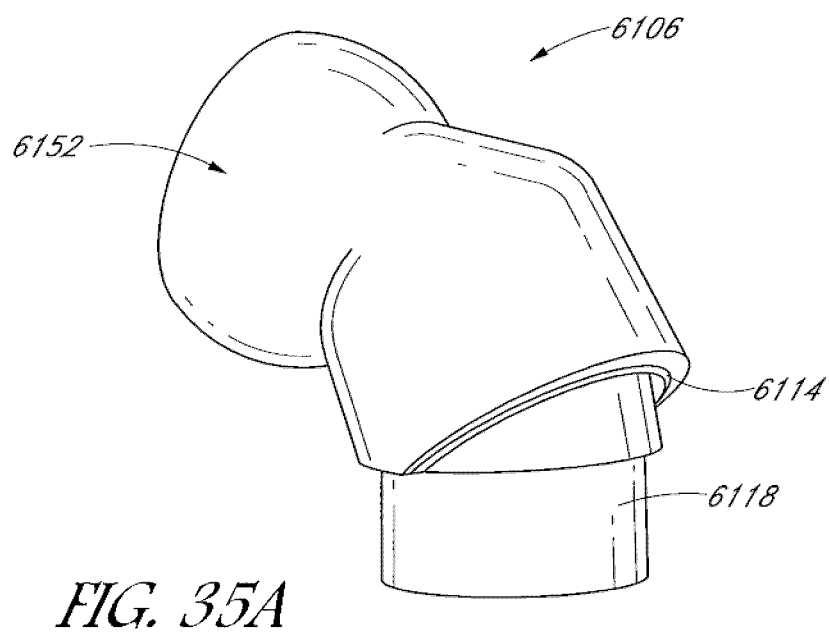
FIG. 35A is a perspective view of a connection port assembly with slots, according to an embodiment of the present disclosure.
Figure 35B:
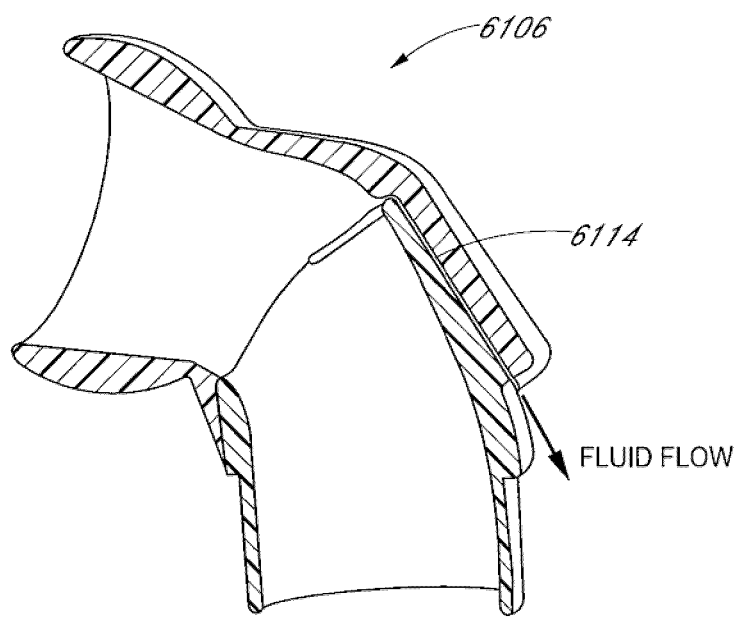
FIG. 35B is a cross-sectional view of the connection port assembly of FIG. 35A.

FIGS. 35A-B illustrate an embodiment having slots 6114 on the connection port assembly 6106. The connection port assembly 6106 has two components. A first component with the ball socket 6152 and a second component with the connection end 6118. When the two components are assembled, a space between the two components can form the slot 6114. The slot 6114 can have the same features as discussed above in other embodiments.

Figure 36E:
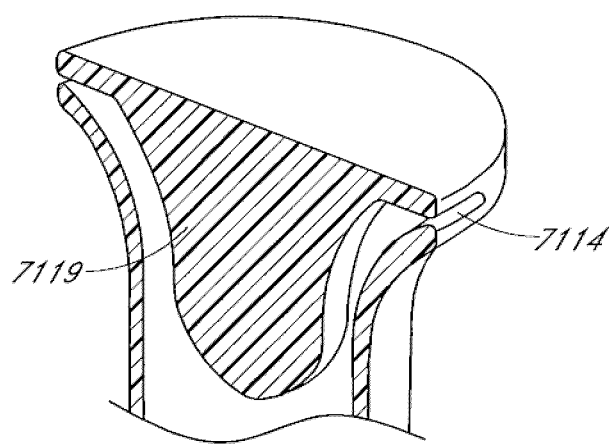

FIGS. 36A-F illustrate various embodiments of slot designs. FIG. 36A illustrates radially outward facing slots 7114 at the end of a flared flow path. As discussed before, the radial direction of the slots can help to reduce the draft effects and disturbance to the user and bed partner. It has been discovered that a slot width of approximately 0.35 mm provides good performance in minimizing the noise levels.

However, in some embodiments, the slot width can be at least approximately 0.2 mm and/or less than or equal to approximately 0.5 mm.

Figure 36F:
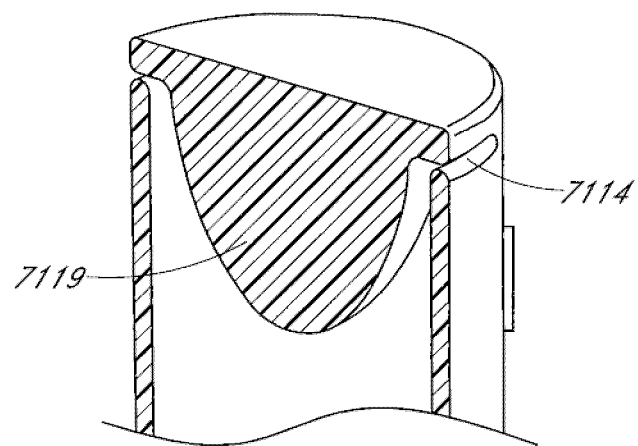

FIG. 36B illustrates radially outward facing slots 7114 at the end of a straight flow path. FIG. 36C illustrates radially inward facing slots 7114 at the end of a bulbous flow path. FIG. 36D illustrates outward facing slots 7114 that are tiered. The illustrated embodiment has three tiers of slots 7114. In other embodiments, there can be one, two or more than three tiers. FIG. 36E illustrates slots 7114 at the end of a flared flow path which includes an internal curve 7119. The internal curve can encourage the flow direction out through the slots rather than flowing into a capped surface. The internal curve can provide a smoother fluid flow, which can result in reduced noise levels. FIG. 36F illustrates radially outward facing slots 7114 at the end of a straight flow path which includes an internal curve 7119.

Although certain embodiments, features, and examples have been described herein, it will be understood by those skilled in the art that many aspects of the methods and devices illustrated and described in the present disclosure may be differently combined and/or modified to form still further embodiments. For example, any one component of the interface illustrated and described above can be used alone or with other components without departing from the spirit of the present invention. Additionally, it will be recognized that the methods described herein may be practiced in different sequences, and/or with additional devices as desired. Such alternative embodiments and/or uses of the methods and devices described above and obvious modifications and equivalents thereof are intended to be included within the scope of the present invention. Thus, it is intended that the scope of the present invention should not be limited by the particular embodiments described above, but should be determined only by a fair reading of the claims that follow.

What is claimed is:

1. A patient interface comprising:
    a body portion sized and shaped to surround a nose and/or a mouth of a user and adapted to create at least a substantial seal with a face of the user;
    an unsealed frame portion to be held in place by a headgear assembly configured to wrap around a head of the user, wherein the unsealed frame portion is at least partially spaced away from the face of the user and comprises a plurality of headgear connectors configured to connect to the headgear assembly, the body portion adapted to be secured to the frame portion;
    a coupling that permits the patient interface to be coupled to a gas delivery system;
    a vent that allows a flow of vented gases to move from an interior of the body portion to an exterior of the body portion, the vent comprising a plurality of exit holes arranged in an array; and
    wherein the frame portion and the body portion cooperate to define a plenum chamber between them, wherein the frame portion is positioned in front of the body portion such that the flow of the vented gases moves into the plenum chamber through the plurality of exit holes and from the plenum chamber into the environment through a space between the frame portion and the user's face.

2. The patient interface of claim 1, wherein a diameter of each of the plurality of exit holes is between about 0.5 mm and about 1.5 mm.

3. The patient interface of claim 1, wherein a length to diameter ratio of each of the plurality of exit holes is at least about 2.

4. The patient interface of claim 1, wherein a ratio of a pitch distance between each of the plurality of exit holes to a diameter of each of the plurality of exit holes is at least about 4.

5. The patient interface of claim 1, wherein an exit radius of each of the plurality of exit holes is at least about 0.5 mm and/or an entry radius of each of the plurality of exit holes is at least about 0.5 mm.

6. The patient interface of claim 1, wherein the coupling is a ball-jointed elbow or a swiveling joint.

7. The patient interface of claim 1, wherein the plenum chamber is configured to reduce a draft and noise from the vent by enabling an energy present in the flow of vented gases to dissipate.

8. The patient interface of claim 1, wherein the coupling is separate from the body portion and the frame portion and coupled to one of the body portion and the frame portion.

9. The patient interface of claim 8, wherein the coupling is releasably connected to the one of the body portion and the frame portion.

10. The patient interface of claim 8, wherein the coupling has an exterior end configured to connect to a breathing tube.

11. The patient interface of claim 1, wherein the frame portion comprises a forehead rest having a contact portion configured to contact a forehead of the user in use, wherein a remainder of the frame portion is configured to be spaced from the face of the user in use.

12. A patient interface comprising:
    a body portion sized and shaped to surround a nose and/or a mouth of a user and adapted to create at least a substantial seal with a face of the user;
    a frame portion to be held in place by a headgear assembly, wherein the frame portion comprises a plurality of headgear connectors configured to connect to the headgear assembly, wherein the body portion is adapted to be secured to the frame portion;
    a coupling that permits the patient interface to be coupled to a gas delivery system;
    a vent that allows a flow of vented gas to move from an interior of the body portion to an exterior of the body portion, the vent comprising a plurality of exit holes arranged in an array;
    wherein the frame portion and the body portion cooperate to define a plenum chamber between them, wherein the frame portion is positioned in front of the body portion such that the flow of the vented gas moves into the plenum chamber through the plurality of exit holes, wherein at least a portion of a perimeter of the frame portion is configured to be spaced from the face of the user such that the flow of vented gas moves from the plenum chamber into the environment through a space between the frame portion and the user's face.

13. The patient interface of claim 12, wherein a diameter of each of the plurality of exit holes is between about 0.5 mm and about 1.5 mm.

14. The patient interface of claim 12, wherein a length to diameter ratio of each of the plurality of exit holes is at least about 2.

15. The patient interface of claim 12, wherein a ratio of a pitch distance between each of the plurality of exit holes to a diameter of each of the plurality of the exit holes is at least about 4.

16. The patient interface of claim 12, wherein an exit radius of each of the plurality of exit holes is at least about 0.5 mm and/or an entry radius of each of the plurality of exit holes is at least about 0.5 mm.

17. A patient interface assembly, comprising:
a first portion configured to deliver respiratory gases to at least a nose and/or a mouth of a user, the first portion having a first surface;
a second portion adapted to be positioned in front of and connected to the first portion, the second portion having a second surface, wherein the second surface faces the first surface, the second portion defining a perimeter, wherein at least a portion of the perimeter is configured to be spaced away from a face of the user;
a coupling that permits the patient interface to be coupled to a gas delivery system, wherein the first portion comprises a first opening and the second portion comprises a second opening, and a flow of breathing gases can pass through the first opening and the second opening to be delivered to the nose and/or the mouth of the user;
a headgear assembly configured to wrap around the user's head and secure the first portion and the second portion in place relative to the face of the user;
a vent that allows a flow of vented gases to move from an interior to an exterior of the first portion, the vent comprising a plurality of exit holes formed in the first portion;
a plenum chamber at least partially defined between the first surface and the second surface, wherein the flow of the vented gases moves into the plenum chamber through the plurality of exit holes and from the plenum chamber into the environment through a space between the first portion and the portion of the perimeter of the second portion that is spaced away from the face of the user.

18. The patient interface assembly of claim 17, wherein the plenum chamber is configured to reduce a draft and noise from the vent by enabling energy present in the flow of the vented gases to dissipate.

19. The patient interface assembly of claim 17, wherein a diameter of each of the plurality of exit holes is between about 0.5 mm and about 1.5 mm.

20. The patient interface assembly of claim 17, wherein a length to diameter ratio of each of the plurality of exit holes is at least about 2.

21. The patient interface assembly of claim 17, wherein a ratio of a pitch distance between each of the plurality of exit holes to a diameter of each of the plurality of exit holes is at least about 4.

22. The patient interface assembly of claim 17, wherein an exit radius of each of the plurality of exit holes is at least about 0.5 mm and/or an entry radius of each of the plurality of exit holes is at least about 0.5 mm.

23. The patient interface assembly of claim 17, wherein the coupling is a ball-jointed elbow or a swiveling joint.

24. The patient interface assembly of claim 17, wherein the coupling is separate from the first portion and the second portion and is coupled to one of the first portion and the second portion.

25. The patient interface assembly of claim 24, wherein the coupling is releasably coupled to the one of the first portion and the second portion.

26. The patient interface assembly of claim 17, wherein the coupling has an exterior end configured to connect to a breathing tube.

27. The patient interface assembly of claim 17, wherein an engagement region between the first portion and the second portion is defined by one of the first opening and the second opening and surrounds the other of the first opening and the second opening.

28. A patient interface assembly, comprising:
a body portion configured to deliver respiratory gases to at least a nose and/or a mouth of a user, the body portion having a first surface;
a shroud connected to the body portion, the shroud having a second surface, wherein the second surface faces the first surface, the shroud positioned in front of at least a portion of the body portion and defining a perimeter, wherein at least a portion of the perimeter is configured to be spaced away from a face of the user and from the body portion, wherein a space is defined between the body portion and the perimeter of the shroud;
a coupling that permits the patient interface to be coupled to a gas delivery system;
a headgear assembly configured to wrap around a head of the user and secure the body portion in place on the face of the user;
a vent that allows a flow of vented gases to move from an interior to an exterior of the body portion, the vent comprising a plurality of exit holes formed in the body portion;
a plenum chamber defined between the first surface and the second surface, wherein the flow of the vented gases moves into the plenum chamber through the plurality of exit holes and is directed toward the second surface, and wherein the flow of vented gases is redirected by the second surface to exit the plenum chamber into the environment through the space between the body portion and the shroud.

29. The patient interface assembly of claim 28, wherein the plenum chamber is configured to reduce a draft and noise from the vent by enabling energy present in the flow of the vented gases to dissipate.

30. The patient interface assembly of claim 28, wherein a diameter of each of the plurality of exit holes is between about 0.5 mm and about 1.5 mm.

31. The patient interface assembly of claim 28, wherein a length to diameter ratio of each of the plurality of exit holes is at least about 2.

32. The patient interface assembly of claim 28, wherein a ratio of a pitch distance between each of the plurality of exit holes a diameter of each of the plurality of exit holes is at least about 4.

33. The patient interface assembly of claim 28, wherein an exit radius of each of the plurality of exit holes is at least about 0.5 mm and/or an entry radius of each of the plurality of exit holes is at least about 0.5 mm.

34. The patient interface assembly of claim 28, wherein each of the plurality of exit holes defines a hole diameter, wherein the second surface is positioned between about 3 to about 5 hole diameters from the first surface.

35. The patient interface assembly of claim 28, wherein the coupling is a ball-jointed elbow or a swiveling joint.

36. The patient interface assembly of claim 28, wherein the coupling is separate from the body portion and the shroud and is coupled to one of the body portion and the shroud.

37. The patient interface assembly of claim 36, wherein the coupling is releasably connected to the one of the body portion and the shroud.

38. The patient interface assembly of claim 28, wherein the coupling has an exterior end configured to connect to a breathing tube.

39. The patient interface assembly of claim 28, wherein the body portion comprises a first opening and the shroud comprises a second opening, wherein a flow of breathing gases can pass through the first opening and the second opening to be delivered to the nose and/or the mouth of the user.

40. The patient interface assembly of claim 39, wherein a connection region between the body portion and the shroud is defined by one of the first opening and the second opening.

41. The patient interface assembly of claim 40, wherein the connection region surrounds the other of the first opening and the second opening.

* * * * *